United States Patent [19]

Bell et al.

[11] Patent Number: 4,793,995

[45] Date of Patent: Dec. 27, 1988

[54] MODIFIED (1-56) BETA INTERFERONS

[75] Inventors: Leslie D. Bell, Thame; John C. Smith; Paul G. Boseley, both of High Wycombe, all of United Kingdom

[73] Assignee: G. D. Searle & Co., Chicago, Ill.

[21] Appl. No.: 623,815

[22] Filed: Jun. 22, 1984

[30] Foreign Application Priority Data

Jul. 1, 1983 [GB] United Kingdom ............... 8317880

[51] Int. Cl.[4] ............ A61K 45/02; C07K 13/00; C07K 15/26; C12P 21/00
[52] U.S. Cl. ............ 424/85.6; 530/351; 435/68; 435/811; 435/172.3
[58] Field of Search ............ 435/68, 172.3; 424/85; 530/351

[56] References Cited

U.S. PATENT DOCUMENTS

| 4,414,150 | 8/1983 | Goeddel | 435/70 |
| 4,569,908 | 2/1986 | Mark et al. | 435/71 |
| 4,588,585 | 5/1986 | Mark et al. | 435/172.3 |

OTHER PUBLICATIONS

Shepard et al. Nature, vol. 294, pp. 563-565, 1981.

*Primary Examiner*—Blondel Hazel
*Attorney, Agent, or Firm*—Mary Jo Kanady; Paul D. Matukaitis

[57] ABSTRACT

Modified beta interferons containing amino acid substitutions in the beta interferon amino acids 1 to 56 are described. These modified beta interferons exhibit changes in the antiviral, cell growth regulatory or immunomodulatory activities when compared with unmodified beta interferon.

17 Claims, 3 Drawing Sheets

FIG. 2a

Chemically synthesized sequence for IFNX487

HinfI
ATTCCATTCTCTCGACAACAGACGTACCCTTATGCTGCTCGCTCAGATGAGCCGGATATCCCC
    GGTAAGAGAGCTGTTGTCTGCATGGGAATACGACGAGCGAGTCTACTCGGCCTATAGGGG GTCTTCTTGCCTGATGGACCGCCACGACTTCGGCTTCCCTCAGGAAGAATTCGATGGCAATCA
CAGAAGAACGGACTACCTGGCGGTGCTGAAGCCGAAGGGAGTCCTTCTTAAGCTACCGTTAGT GTTTCAGAAAGCACCTGCGATTC
CAAAGTCTTTCGTGGACGCTAAGACTGG
                HgaI

FIG.2b

Chemically synthesized sequence for IFNX410

ClaI

CGATAAGCTATGTGCGACTTACCACAATTCCATTCTCTCGACAACCGTCGTACTCTGATGCTG
 TATTCGATACACGCTGAATGGTGTTAAGGTAAGAGAGCTGTTGGCAGCATGAGACTACGAC

CTCGCTCAGATGAGCCGGATATCCCCGTCTTCTTGCCTGATGGACCGCCACGACTTCGGCTTC
GAGCGAGTCTACTCGGCCTATAGGGGCAGAAGAACGGACTACCTGGCGGTGCTGAAGCCGAAG

CCTCAGGAAGAATTCGATGGCAATCAGTTTCAGAAAGCACCTGCGATTCTGACCATCTACGAA
GGAGTCCTTCTTAAGCTACCGTTAGTCAAAGTCTTTCGTGGACGCTAAGACTGGTAGATGCTT

ATGCTGCAAAACATCTTCG
TACGACCTTTTGTAGAAGC
               NruI

FIG.2c

Chemically synthesized oligonucleotide for IFNX415

<u>ClaI</u>
CGATAAGCTATGAGCTACAACTTGCTTGGATTCCTACAAAGAAGCAGCAATTTTCAGTCTCAG
 TATTCGATACTCGATGTTGAACGAACCTAAGGATGTTTCTTCGTCGTTAAAAGTCAGAGTC

AAGCTCCTGTGGCAATTGAATGGGAGGTCTTGCCTGAAGGACCGCCACGACTTCGGCTTCCCT
TTCGAGGACACCGTTAACTTACCCTCCAGAACGGACTTCCTGGCGGTGCTGAAGCCGAAGGGA

CAGGAAGAATTCGATGGCAATCTGCAGCAGTTTCAGAAAGAGGACGCCGCATTGACCATCTAT
GTCCTTCTTAAGCTACCGTTAGACGTCGTCAAAGTCTTTCTCCTGCGGCGTAACTGGTAGATA

GAGATGCTCCAGAACATCTTTGCTATTTTCAGACAAGATTCC
CTCTACGAGGTCTTGTAGAAACGATAAAAGTCTGTTCTAAGGAGCT
                                                        <u>XhoI</u>

FIG. 2d

Chemically synthesized sequence for IFNX492

```
 HinfI                    RsaI
 ATTCCATTCTCTCGACAACAGACGTACCTGTATGCTGCTCGCTCAGATGAGCCGGATATCCC
     GGTAAGAGAGCTGTTGTCTGCATGGACATACGACGAGCGAGTCTACTCGGCCTATAGGG EcoRI
 CGTCTTCTTGCCTGATGGACCGCCACGACTTCGGCTTCCCTCAGGAAGAATTCGATGGCAATC
 GCAGAAGAACGGACTACCTGGCGGTGCTGAAGCCGAAGGGAGTCCTTCTTAAGCTACCGTTAG HgaI
 AGTTTCAGAAAGCACCTGCGATTC
 TCAAAGTCTTTCGTGGACGCTAAGACTGG
```

FIG. 2e

Chemically synthesized sequence for IFNX419

ClaI
CGATAAGCTATGTCTTACAACCTGCTGGGCTTCCATTCTCTGGACAACCGTCGTACTCTGATG
  TATTCGATACAGAATGTTGGACGACCCGAAGGTAAGAGACCTGTTGGCAGCATGAGACTAC

CTGCTCGCTCAGATGAGCCGGATATCCCCGTCTTCTTGCCTGATGGACCGCCACGACTTCGGC
GACGAGCGAGTCTACTCGGCCTATAGGGGCAGAAGAACGGACTACCTGGCGGTGCTGAAGCCG

TTCCCTCAGGAAATCAAACAG
AAGGGAGTCCTTTAGTTTGTC
                PvuII

FIG. 2f

Chemically synthesized sequence for IFNX42β

```
ClaI
CGATAAGCTATGTCTTACAACCTGCTGGGCTTCCTGCAGCGTTCTTCTAACTTCCAATCTCAG
  TATTCGATACAGAATGTTGGACGACCCGAAGGACGTCGCAAGAAGATTGAAGGTTAGAGTC

AAACTGGCTCAGATGAGCCGGATATCCCCGTCTTCTTGCCTGATGGACCGCCACGACTTCGGC
TTTGACCGAGTCTACTCGGCCTATAGGGGCAGAAGAACGGACTACCTGGCGGTGCTGAAGCCG

TTCCCTCAGGAAATCAAACAG
AAGGGAGTCCTTTAGTTTGTC
                PvuII
```

FIG.2g

Chemically synthesized sequence for IFNX404

DdeI                                                    HgaI
TGAGGAAGAGTTTGACGGTAATCAGTTCCAAAAAGCCCCAGCAATCT
    CCTTCTCAAACTGCCATTAGTCAAGGTTTTTCGGGGTCGTTAGAACTGG

FIG.3a

IFNX407

IFN-β[IFN-β$^{9-56}$→IFN-α$_1$$^{7-54}$]

```
                         HinfI
                           ↓
              5                     10                  15
MET SER TYR ASN LEU LEU GLY PHE HIS SER LEU ASP ASN ARG ARG
ATG AGC TAC AAC TTG CTT GGA TTC CAT TCT CTC GAC AAC AGA CGT 20                    25                  30
THR LEU MET LEU LEU ALA GLN MET SER ARG ILE SER PRO SER SER
ACC CTT ATG CTG CTC GCT CAG ATG AGC CGG ATA TCC CCG TCT TCT 35                    40                  45
CYS LEU MET ASP ARG HIS ASP PHE GLY PHE PRO GLN GLU GLU PHE
TGC CTG ATG GAC CGC CAC GAC TTC GGC TTC CCT CAG GAA GAA TTC HgaI
              50                    55          ↓      60
ASP GLY ASN GLN PHE GLN LYS ALA PRO ALA ILE LEU THR ILE TYR
GAT GGC AAT CAG TTT CAG AAA GCA CCT GCG ATT CTG ACC ATC TAT 65                    70                  75
GLU MET LEU GLN ASN ILE PHE ALA ILE PHE ARG GLN ASP SER SER
GAG ATG CTC CAG AAC ATC TTT GCT ATT TTC AGA CAA GAT TCA TCT 80                    85                  90
SER THR GLY TRP ASN GLU THR ILE VAL GLU ASN LEU LEU ALA ASN
AGC ACT GGC TGG AAT GAG ACT ATT GTT GAG AAC CTC CTG GCT AAT 95                    100                 105
VAL TYR HIS GLN ILE ASN HIS LEU LYS THR VAL LEU GLU GLU LYS
GTC TAT CAT CAG ATA AAC CAT CTG AAG ACA GTC CTG GAA GAA AAA 110                   115                 120
LEU GLU LYS GLU ASP PHE THR ARG GLY LYS LEU MET SER SER LEU
CTG GAG AAA GAA GAT TTC ACC AGG GGA AAA CTC ATG AGC AGT CTG 125                   130                 135
HIS LEU LYS ARG TYR TYR GLY ARG ILE LEU HIS TYR LEU LYS ALA
CAC CTG AAA AGA TAT TAT GGG AGG ATT CTG CAT TAC CTG AAG GCC 140                   145                 150
LYS GLU TYR SER HIS CYS ALA TRP THR ILE VAL ARG VAL GLU ILE
AAG GAG TAC AGT CAC TGT GCC TGG ACC ATA GTC AGA GTG GAA ATC 155                   160                 165
LEU ARG ASN PHE TYR PHE ILE ASN ARG LEU THR GLY TYR LEU ARG
CTA AGG AAC TTT TAC TTC ATT AAC AGA CTT ACA GGT TAC CTC CGA

ASN ***
AAC TGA
```

FIG. 3a(CONT'D.)

```
        10         20         30         40         50
MYSNLLGFHS-LDNRRTLMLL-AQMSRISPSS-CLMDRHDFGF-PQEEFDGNQF- 60         70         80         90        100
QKAPAILTIY-EMLQNIFAIF-RQDSSSTGWN-ETIVENLLAN-VYHQINHLKT- 110        120        130        140        150
VLEEKLEKED-FTRGKLMSSL-HLKRYYGRIL-HYLKAKEYSH-CAWTIVRVEI-

160
LRNFYFINRL-TGYLRN<
```

FIG. 3b

IFNX408

$\text{IFN-}\beta[\text{IFN-}\beta^{44-56} \rightarrow \text{IFN-}\alpha_1^{42-54}][\text{Cys}^{17} \rightarrow \text{Ser}^{17}]$

```
                      5                          10                         15
    MET SER TYR ASN LEU LEU GLY PHE LEU GLN ARG SER SER ASN PHE
    ATG AGC TAC AAC TTG CTT GGA TTC CTA CAA AGA AGC AGC AAT TTT

T
        |
        V           20                         25                         30
    GLN SER GLN LYS LEU LEU TRP GLN LEU ASN GLY ARG LEU GLU TYR
    CAG AGT CAG AAG CTC CTG TGG CAA TTG AAT GGG AGG CTT GAA TAC 35                         40                         45
    CYS LEU LYS ASP ARG MET ASN PHE ASP ILE PRO GLU GLU GLU PHE
    TGC CTC AAG GAC AGG ATG AAC TTT GAC ATC CCT GAG GAA GAG TTT 50                         55                         60
    ASP GLY ASN GLN PHE GLN LYS ALA PRO ALA ILE LEU THR ILE TYR
    GAC GGT AAT CAG TTC CAA AAA GCC CCA GCA ATC TTG ACC ATC TAT 65                         70                         75
    GLU MET LEU GLN ASN ILE PHE ALA ILE PHE ARG GLN ASP SER SER
    GAG ATG CTC CAG AAC ATC TTT GCT ATT TTC AGA CAA GAT TCA TCT 80                         85                         90
    SER THR GLY TRP ASN GLU THR ILE VAL GLU ASN LEU LEU ALA ASN
    AGC ACT GGC TGG AAT GAG ACT ATT GTT GAG AAC CTC CTG GCT AAT 95                        100                        105
    VAL TYR HIS GLN ILE ASN HIS LEU LYS THR VAL LEU GLU GLU LYS
    GTC TAT CAT CAG ATA AAC CAT CTG AAG ACA GTC CTG GAA GAA AAA 110                        115                        120
    LEU GLU LYS GLU ASP PHE THR ARG GLY LYS LEU MET SER SER LEU
    CTG GAG AAA GAA GAT TTC ACC AGG GGA AAA CTC ATG AGC AGT CTG 125                        130                        135
    HIS LEU LYS ARG TYR TYR GLY ARG ILE LEU HIS TYR LEU LYS ALA
    CAC CTG AAA AGA TAT TAT GGG AGG ATT CTG CAT TAC CTG AAG GCC 140                        145                        150
    LYS GLU TYR SER HIS CYS ALA TRP THR ILE VAL ARG VAL GLU ILE
    AAG GAG TAC AGT CAC TGT GCC TGG ACC ATA GTC AGA GTG GAA ATC 155                        160                        165
    LEU ARG ASN PHE TYR PHE ILE ASN ARG LEU THR GLY TYR LEU ARG
    CTA AGG AAC TTT TAC TTC ATT AAC AGA CTT ACA GGT TAC CTC CGA

ASN ***
    AAC TGA
```

FIG. 3b (CONT'D.)

```
        10         20         30         40         50
MSYNLLGFLQ-RSSNFQSQKL-LWQLNGRLEY-CLKDRMNFDI-PEEEFDGNQF- 60         70         80         90        100
QKAPAILTIY-EMLQNIFAIF-RQDSSSTGWN-ETIVENLLAN-VYHQINHLKT- 110        120        130        140        150
VLEEKLEKED-FTRGKLMSSL-HLKRYYGRIL-HYLKAKEYSH-CAWTIVRVEI-

160
LRNFYFINRL-TGYLRN<
```

FIG.3c

IFNX409

IFN-β[IFN-β$^{42-56}$->IFN-α$_1$$^{40-54}$][Cys$^{17}$->Ser$^{17}$]

```
                    5                        10                       15
    MET SER TYR ASN LEU LEU GLY PHE LEU GLN ARG SER SER ASN PHE
    ATG AGC TAC AAC TTG CTT GGA TTC CTA CAA AGA AGC AGC AAT TTT 20                        25                       30
    GLN SER GLN LYS LEU LEU TRP GLN LEU ASN GLY ARG LEU GLU TYR
    CAG AGT CAG AAG CTC CTG TGG CAA TTG AAT GGG AGG CTT GAA TAC

G   G  (IFNX408)
                                                  |   |
                   35                        40   v   v               45
    CYS LEU LYS ASP ARG MET ASN PHE ASP ILE PRO GLN GLU GLU PHE
    TGC CTC AAG GAC AGG ATG AAC TTT GAC ATC CCT CAA GAA GAG TTT 50                        55                       60
    ASP GLY ASN GLN PHE GLN LYS ALA PRO ALA ILE LEU THR ILE TYR
    GAC GGT AAT CAG TTC CAA AAA GCC CCA GCA ATC TTG ACC ATC TAT 65                        70                       75
    GLU MET LEU GLN ASN ILE PHE ALA ILE PHE ARG GLN ASP SER SER
    GAG ATG CTC CAG AAC ATC TTT GCT ATT TTC AGA CAA GAT TCA TCT 80                        85                       90
    SER THR GLY TRP ASN GLU THR ILE VAL GLU ASN LEU LEU ALA ASN
    AGC ACT GGC TGG AAT GAG ACT ATT GTT GAG AAC CTC CTG GCT AAT 95                       100                      105
    VAL TYR HIS GLN ILE ASN HIS LEU LYS THR VAL LEU GLU GLU LYS
    GTC TAT CAT CAG ATA AAC CAT CTG AAG ACA GTC CTG GAA GAA AAA 110                       115                      120
    LEU GLU LYS GLU ASP PHE THR ARG GLY LYS LEU MET SER SER LEU
    CTG GAG AAA GAA GAT TTC ACC AGG GGA AAA CTC ATG AGC AGT CTG 125                       130                      135
    HIS LEU LYS ARG TYR TYR GLY ARG ILE LEU HIS TYR LEU LYS ALA
    CAC CTG AAA AGA TAT TAT GGG AGG ATT CTG CAT TAC CTG AAG GCC 140                       145                      150
    LYS GLU TYR SER HIS CYS ALA TRP THR ILE VAL ARG VAL GLU ILE
    AAG GAG TAC AGT CAC TGT GCC TGG ACC ATA GTC AGA GTG GAA ATC 155                       160                      165
    LEU ARG ASN PHE TYR PHE ILE ASN ARG LEU THR GLY TYR LEU ARG
    CTA AGG AAC TTT TAC TTC ATT AAC AGA CTT ACA GGT TAC CTC CGA

ASN ***
    AAC TGA
```

FIG. 3c (CONT'D.)

```
        10         20         30         40         50
MSYNLLGFLQ-RSSNFQSQKL-LWQLNGRLEY-CLKDRMNFDI-PQEEFDGNQF- 60         70         80         90        100
QKAPAILTIY-EMLQNIFAIF-RQDSSSTGWN-ETIVENLLAN-VYHQINHLKT- 110        120        130        140        150
VLEEKLEKED-FTRGKLMSSL-HLKRYYGRIL-HYLKAKEYSH-CAWTIVRVEI-

160
LRNFYFINRL-TGYLRN<
```

FIG.3d

IFNX410

IFN-β[IFN-$β^{2-7}$->IFN-$α_2^{1-5}$] [IFN-$β^{9-56}$->IFN-$α_1^{7-54}$]

```
   ClaI
  ┌─                      5                      10                       15
  │   MET CYS ASP LEU PRO GLN PHE HIS SER LEU ASP ASN ARG ARG THR
(N9) ATG TGC GAC TTA CCA CAA TTC CAT TCT CTC GAC AAC CGT CGT ACT 20                      25                       30
      LEU MET LEU LEU ALA GLN MET SER ARG ILE SER PRO SER SER CYS
      CTG ATG CTG CTC GCT CAG ATG AGC CGG ATA TCC CCG TCT TCT TGC 35                      40                       45
      LEU MET ASP ARG HIS ASP PHE GLY PHE PRO GLN GLU GLU PHE ASP
      CTG ATG GAC CGC CAC GAC TTC GGC TTC CCT CAG GAA GAA TTC GAT 50                      55                       60
      GLY ASN GLN PHE GLN LYS ALA PRO ALA ILE LEU THR ILE TYR GLU
      GGC AAT CAG TTT CAG AAA GCA CCT GCG ATT CTG ACC ATC TAC GAA

NruI
                         65       ↓            70                       75
      MET LEU GLN ASN ILE PHE ALA ILE PHE ARG GLN ASP SER SER SER
      ATG CTG CAA AAC ATC TTC GCG ATC TTC CGT CAA GAC TCT TCC TCT 80                      85                       90
      THR GLY TRP ASN GLU THR ILE VAL GLU ASN LEU LEU ALA ASN VAL
      ACT GGT TGG AAC GAA ACT ATC GTA GAA AAC CTG CTG GCA AAC GTA 95                     100                      105
      TYR HIS GLN ILE ASN HIS LEU LYS THR VAL LEU GLU GLU LYS LEU
      TAC CAT CAG ATC AAC CAT CTG AAA ACC GTG CTG GAA GAG AAA CTG 110                     115                      120
      GLU LYS GLU ASP PHE THR ARG GLY LYS LEU MET SER SER LEU HIS
      GAA AAA GAA GAC TTC ACC CGC GGT AAA CTG ATG AGC TCC CTG CAT 125                     130                      135
      LEU LYS ARG TYR TYR GLY ARG ILE LEU HIS TYR LEU LYS ALA LYS
      CTG AAA CGC TAC TAT GGT CGT ATC CTG CAT TAC CTG AAA GCT AAA 140                     145                      150
      GLU TYR SER HIS CYS ALA TRP THR ILE VAL ARG VAL GLU ILE LEU
      GAA TAC TCT CAC TGC GCA TGG ACT ATT GTA CGC GTT GAA ATC CTG 155                     160                      165
      ARG ASN PHE TYR PHE ILE ASN ARG LEU THR GLY TYR LEU ARG ASN
      CGT AAC TTC TAC TTC ATC AAC CGC CTG ACT GGT TAC CTG CGT AAC

***
      TAA
```

FIG. 3d (CONT'D.)

```
        10         20         30         40         50
MCDLPQFHSL-DNRRTLMLLA-QMSRISPSSC-LMDRHDFGFP-QEEFDGNQFQ- 60         70         80         90        100
KAPAILTIYE-MLQNIFAIFR-QDSSSTGWNE-TIVENLLANV-YHQINHLKTV- 110        120        130        140        150
LEEKLEKEDF-TRGKLMSSLH-LKRYYGRILH-YLKAKEYSHC-AWTIVRVEIL-

160
RNFYFINRLT-GYLRN<
```

FIG.3e

IPNX415

IFN-β[IFN-β$^{28-46}$->IFN-$\alpha_1^{28-46}$][Cys$^{17}$->Ser$^{17}$][Met$^{31}$->Lys$^{31}$]

```
     ClaI
  ┌──              5                    10                   15
  │     MET SER TYR ASN LEU LEU GLY PHE LEU GLN ARG SER SER ASN PHE
(N9)    ATG AGC TAC AAC TTG CTT GGA TTC CTA CAA AGA AGC AGC AAT TTT 20                   25                   30
        GLN SER GLN LYS LEU LEU TRP GLN LEU ASN GLY ARG SER CYS LEU
        CAG TCT CAG AAG CTC CTG TGG CAA TTG AAT GGG AGG TCT TGC CTG 35                   40                   45
        LYS ASP ARG HIS ASP PHE GLY PHE PRO GLN GLU GLU PHE ASP GLY
        AAG GAC CGC CAC GAC TTC GGC TTC CCT CAG GAA GAA TTC GAT GGC 50                   55                   60
        ASN LEU GLN GLN PHE GLN LYS GLU ASP ALA ALA LEU THR ILE TYR
        AAT CTG CAG CAG TTT CAG AAA GAG GAC GCC GCA TTG ACC ATC TAT

XhoI
                    65                   70              ↓   75
        GLU MET LEU GLN ASN ILE PHE ALA ILE PHE ARG GLN ASP SER SER
        GAG ATG CTC CAG AAC ATC TTT GCT ATT TTC AGA CAA GAT TCC TCG 80                   85                   90
        SER THR GLY TRP ASN GLU THR ILE VAL GLU ASN LEU LEU ALA ASN
        AGC ACT GGC TGG AAT GAG ACT ATT GTT GAG AAC CTC CTG GCT AAT 95                   100                  105
        VAL TYR HIS GLN ILE ASN HIS LEU LYS THR VAL LEU GLU GLU LYS
        GTC TAT CAT CAG ATA AAC CAT CTG AAG ACA GTC CTG GAA GAA AAA 110                  115                  120
        LEU GLU LYS GLU ASP PHE THR ARG GLY LYS LEU MET SER SER LEU
        CTG GAG AAA GAA GAT TTC ACC AGG GGA AAA CTC ATG AGC AGT CTG 125                  130                  135
        HIS LEU LYS ARG TYR TYR GLY ARG ILE LEU HIS TYR LEU LYS ALA
        CAC CTG AAA AGA TAT TAT GGG AGG ATT CTG CAT TAC CTG AAG GCC 140                  145                  150
        LYS GLU TYR SER HIS CYS ALA TRP THR ILE VAL ARG VAL GLU ILE
        AAG GAG TAC AGT CAC TGT GCC TGG ACC ATA GTC AGA GTG GAA ATC 155                  160                  165
        LEU ARG ASN PHE TYR PHE ILE ASN ARG LEU THR GLY TYR LEU ARG
        CTA AGG AAC TTT TAC TTC ATT AAC AGA CTT ACA GGT TAC CTC CGA

ASN ***
        AAC TGA
```

FIG.3e(CONT'D.)

```
        10         20         30         40         50
MSYNLLGFLQ-RSSNFQSQKL-LWQLNGRSCL-KDRHDFGFPQ-EEFDGNLQQF- 60         70         80         90        100
QKEDAALTIY-EMLQNIFAIF-RQDSSSTGWN-ETIVENLLAN-VYHQINHLKT- 110        120        130        140        150
VLEEKLEKED-FTRGKLMSSL-HLKRYYGRIL-HYLKAKEYSH-CAWTIVRVEI-

160
LRNFYFINRL-TGYLRN<
```

FIG. 3f

IFNX402

IFN-β[β$^{9-56}$→α$_1^{7-54}$][Leu$^{17}$→Cys$^{17}$]

```
                            5          HinfI        10                     15
          MET SER TYR ASN LEU LEU GLY  ↓   PHE HIS SER LEU ASP ASN ARG ARG
          ATG AGC TAC AAC TTG CTT GGA TTC CAT TCT CTC GAC AAC AGA CGT 20                      25                     30
          THR CYS MET LEU LEU ALA GLN MET SER ARG ILE SER PRO SER SER
          ACC TGT ATG CTG CTC GCT CAG ATG AGC CGG ATA TCC CCG TCT TCT 35                      40                     45
          CYS LEU MET ASP ARG HIS ASP PHE GLY PHE PRO GLN GLU GLU PHE
          TGC CTG ATG GAC CGC CAC GAC TTC GGC TTC CCT CAG GAA GAA TTC HgaI
                           50                      55            ↓       60
          ASP GLY ASN GLN PHE GLN LYS ALA PRO ALA ILE LEU THR ILE TYR
          GAT GGC AAT CAG TTT CAG AAA GCA CCT GCG ATT CTG ACC ATC TAT 65                      70                     75
          GLU MET LEU GLN ASN ILE PHE ALA ILE PHE ARG GLN ASP SER SER
          GAG ATG CTC CAG AAC ATC TTT GCT ATT TTC AGA CAA GAT TCA TCT 80                      85                     90
          SER THR GLY TRP ASN GLU THR ILE VAL GLU ASN LEU LEU ALA ASN
          AGC ACT GGC TGG AAT GAG ACT ATT GTT GAG AAC CTC CTG GCT AAT 95                     100                    105
          VAL TYR HIS GLN ILE ASN HIS LEU LYS THR VAL LEU GLU GLU LYS
          GTC TAT CAT CAG ATA AAC CAT CTG AAG ACA GTC CTG GAA GAA AAA 110                     115                    120
          LEU GLU LYS GLU ASP PHE THR ARG GLY LYS LEU MET SER SER LEU
          CTG GAG AAA GAA GAT TTC ACC AGG GGA AAA CTC ATG AGC AGT CTG 125                     130                    135
          HIS LEU LYS ARG TYR TYR GLY ARG ILE LEU HIS TYR LEU LYS ALA
          CAC CTG AAA AGA TAT TAT GGG AGG ATT CTG CAT TAC CTG AAG GCC 140                     145                    150
          LYS GLU TYR SER HIS CYS ALA TRP THR ILE VAL ARG VAL GLU ILE
          AAG GAG TAC AGT CAC TGT GCC TGG ACC ATA GTC AGA GTG GAA ATC 155                     160                    165
          LEU ARG ASN PHE TYR PHE ILE ASN ARG LEU THR GLY TYR LEU ARG
          CTA AGG AAC TTT TAC TTC ATT AAC AGA CTT ACA GGT TAC CTC CGA

ASN ***
          AAC TGA
```

FIG.3f(CONT'D.)

```
        10          20          30          40          50
MSYNLLGFHS-LDNRRTCMLL-AQMSRISPSS-CLMDRHDFGF-PQEEFDGNQF- 60          70          80          90         100
QKAPAILTIY-EMLQNIFAIF-RQDSSSTGWN-ETIVENLLAN-VYHQINHLKT- 110         120         130         140         150
VLEEKLEKED-FTRGKLMSSL-HLKRYYGRIL-HYLKAKEYSH-CAWTIVRVEI-

160
LRNFYFINRL-TGYLRN<
```

FIG.3g

IFNX419

IFN-β[IFN-β$^{9-42}$→IFN-α$_1$$^{7-48}$]

```
    ClaI
              5                        10                        15
    MET SER TYR ASN LEU LEU GLY PHE HIS SER LEU ASP ASN ARG ARG
(N₉) ATG TCT TAC AAC CTG CTG GGC TTC CAT TCT CTG GAC AAC CGT CGT 20                        25                    30
    THR LEU MET LEU LEU ALA GLN MET SER ARG ILE SER PRO SER SER
    ACT CTG ATG CTG CTC GCT CAG ATG AGC CGG ATA TCC CCG TCT TCT 35                        40                        45
    CYS LEU MET ASP ARG HIS ASP PHE GLY PHE PRO GLN GLU ILE LYS
    TGC CTG ATG GAC CGC CAC GAC TTC GGC TTC CCT CAG GAA ATC AAA

PvuII
              50                        55                        60
    GLN LEU GLN GLN PHE GLN LYS GLU ASP ALA ALA LEU THR ILE TYR
    CAG CTG CAA CAG TTC CAA AAA GAA GAT GCA GCG CTG ACT ATC TAC 65                        70                        75
    GLU MET LEU GLN ASN ILE PHE ALA ILE PHE ARG GLN ASP SER SER
    GAA ATG CTG CAA AAC ATC TTC GCG ATC TTC CGT CAA GAC TCT TCC 80                        85                        90
    SER THR GLY TRP ASN GLU THR ILE VAL GLU ASN LEU LEU ALA ASN
    TCT ACT GGT TGG AAC GAA ACT ATC GTA GAA AAC CTG CTG GCA AAC 95                        100                       105
    VAL TYR HIS GLN ILE ASN HIS LEU LYS THR VAL LEU GLU GLU LYS
    GTA TAC CAT CAG ATC AAC CAT CTG AAA ACC GTG CTG GAA GAG AAA 110                       115                       120
    LEU GLU LYS GLU ASP PHE THR ARG GLY LYS LEU MET SER SER LEU
    CTG GAA AAA GAA GAC TTC ACC CGC GGT AAA CTG ATG AGC TCC CTG 125                       130                       135
    HIS LEU LYS ARG TYR TYR GLY ARG ILE LEU HIS TYR LEU LYS ALA
    CAT CTG AAA CGC TAC TAT GGT CGT ATC CTG CAT TAC CTG AAA GCT 140                       145                       150
    LYS GLU TYR SER HIS CYS ALA TRP THR ILE VAL ARG VAL GLU ILE
    AAA GAA TAC TCT CAC TGC GCA TGG ACT ATT GTA CGC GTT GAA ATC 155                       160                       165
    LEU ARG ASN PHE TYR PHE ILE ASN ARG LEU THR GLY TYR LEU ARG
    CTG CGT AAC TTC TAC TTC ATC AAC CGC CTG ACT GGT TAC CTG CGT

ASN ***
    AAC TAA
```

FIG.3g(CONT'D.)

```
        10         20         30         40         50
MSYNLLGFHS-LDNRRTLMLL-AQMSRISPSS-CLMDRHDFGF-PQEIKQLQQF- 60         70         80         90        100
QKEDAALTIY-EMLQNIFAIF-RQDSSTGWN-ETIVENLLAN-VYHQINHLKT- 110        120        130        140        150
VLEEKLEKED-FTRGKLMSSL-HLKRYYGRIL-HYLKAKEYSH-CAWTIVRVEI-

160
LRNFYFINRL-TGYLRN<
```

FIG.3h

IFNX420

IFN-β[IFN-β$^{21-42}$→IFN-α$_1^{19-40}$][Cys$^{17}$→Ser$^{17}$]

```
    ClaI
    ↓                    5                      10                      15
      MET SER TYR ASN LEU LEU GLY PHE LEU GLN ARG SER SER ASN PHE
(N9)  ATG TCT TAC AAC CTG CTG GGC TTT CTG CAG CGT TCT TCT AAC TTC 20                      25                      30
      GLN SER GLN LYS LEU ALA GLN MET SER ARG ILE SER PRO SER SER
      CAA TCT CAG AAA CTG GCT CAG ATG AGC CGG ATA TCC CCG TCT TCT 35                      40                      45
      CYS LEU MET ASP ARG HIS ASP PHE GLY PHE PRO GLN GLU ILE LYS
      TGC CTG ATG GAC CGC CAC GAC TTC GGC TTC CCT CAG GAA ATC AAA

PvuII
      ↓                  50                      55                      60
      GLN LEU GLN GLN PHE GLN LYS GLU ASP ALA ALA LEU THR ILE TYR
      CAG CTG CAA CAG TTC CAA AAA GAA GAT GCA GCG CTG ACT ATC TAC 65                      70                      75
      GLU MET LEU GLN ASN ILE PHE ALA ILE PHE ARG GLN ASP SER SER
      GAA ATG CTG CAA AAC ATC TTC GCG ATC TTC CGT CAA GAC TCT TCC 80                      85                      90
      SER THR GLY TRP ASN GLU THR ILE VAL GLU ASN LEU LEU ALA ASN
      TCT ACT GGT TGG AAC GAA ACT ATC GTA GAA AAC CTG CTG GCA AAC 95                      100                     105
      VAL TYR HIS GLN ILE ASN HIS LEU LYS THR VAL LEU GLU GLU LYS
      GTA TAC CAT CAG ATC AAC CAT CTG AAA ACC GTG CTG GAA GAG AAA 110                     115                     120
      LEU GLU LYS GLU ASP PHE THR ARG GLY LYS LEU MET SER SER LEU
      CTG GAA AAA GAA GAC TTC ACC CGC GGT AAA CTG ATG AGC TCC CTG 125                     130                     135
      HIS LEU LYS ARG TYR TYR GLY ARG ILE LEU HIS TYR LEU LYS ALA
      CAT CTG AAA CGC TAC TAT GGT CGT ATC CTG CAT TAC CTG AAA GCT 140                     145                     150
      LYS GLU TYR SER HIS CYS ALA TRP THR ILE VAL ARG VAL GLU ILE
      AAA GAA TAC TCT CAC TGC GCA TGG ACT ATT GTA CGC GTT GAA ATC 155                     160                     165
      LEU ARG ASN PHE TYR PHE ILE ASN ARG LEU THR GLY TYR LEU ARG
      CTG CGT AAC TTC TAC TTC ATC AAC CGC CTG ACT GGT TAC CTG CGT

ASN ***
      AAC TAA
```

FIG.3h(CONT'D.)

```
        10         20         30         40         50
MSYNLLGFLQ-RSSNFQSQKL-AQMSRISPSS-CLMDRHDFGF-PQEIKQLQQF- 60         70         80         90        100
QKEDAALTIY-EMLQNIFAIF-RQDSSSTGWN-ETIVENLLAN-VYHQINHLKT- 110        120        130        140        150
VLEEKLEKED-FTRGKLMSSL-HLKRYYGRIL-HYLKAKEYSH-CAWTIVRVEI-

160
LRNFYFINRL-TGYLRN<
```

FIG. 3i

IFNX484

IFN-β[IFN-β$^{44-56}$→α$_1^{42-54}$]

```
              5                          10                         15
MET SER TYR ASN LEU LEU GLY PHE LEU GLN ARG SER SER ASN PHE
ATG AGC TAC AAC TTG CTT GGA TTC CTA CAA AGA AGC AGC AAT TTT 20                         25                         30
GLN CYS GLN LYS LEU LEU TRP GLN LEU ASN GLY ARG LEU GLU TYR
CAG TGT CAG AAG CTC CTG TGG CAA TTG AAT GGG AGG CTT GAA TAC 35                         40                         45
CYS LEU LYS ASP ARG MET ASN PHE ASP ILE PRO GLU GLU GLU PHE
TGC CTC AAG GAC AGG ATG AAC TTT GAC ATC CCT GAG GAA GAG TTT 50                         55                         60
ASP GLY ASN GLN PHE GLN LYS ALA PRO ALA ILE LEU THR ILE TYR
GAC GGT AAT CAG TTC CAA AAA GCC CCA GCA ATC TTG ACC ATC TAT 65                         70                         75
GLU MET LEU GLN ASN ILE PHE ALA ILE PHE ARG GLN ASP SER SER
GAG ATG CTC CAG AAC ATC TTT GCT ATT TTC AGA CAA GAT TCA TCT 80                         85                         90
SER THR GLY TRP ASN GLU THR ILE VAL GLU ASN LEU LEU ALA ASN
AGC ACT GGC TGG AAT GAG ACT ATT GTT GAG AAC CTC CTG GCT AAT 95                        100                        105
VAL TYR HIS GLN ILE ASN HIS LEU LYS THR VAL LEU GLU GLU LYS
GTC TAT CAT CAG ATA AAC CAT CTG AAG ACA GTC CTG GAA GAA AAA 110                        115                        120
LEU GLU LYS GLU ASP PHE THR ARG GLY LYS LEU MET SER SER LEU
CTG GAG AAA GAA GAT TTC ACC AGG GGA AAA CTC ATG AGC AGT CTG 125                        130                        135
HIS LEU LYS ARG TYR TYR GLY ARG ILE LEU HIS TYR LEU LYS ALA
CAC CTG AAA AGA TAT TAT GGG AGG ATT CTG CAT TAC CTG AAG GCC 140                        145                        150
LYS GLU TYR SER HIS CYS ALA TRP THR ILE VAL ARG VAL GLU ILE
AAG GAG TAC AGT CAC TGT GCC TGG ACC ATA GTC AGA GTG GAA ATC 155                        160                        165
LEU ARG ASN PHE TYR PHE ILE ASN ARG LEU THR GLY TYR LEU ARG
CTA AGG AAC TTT TAC TTC ATT AAC AGA CTT ACA GGT TAC CTC CGA

ASN ***
AAC TGA
```

FIG. 3i (CONT'D.)

```
         10          20          30          40          50
MSYNLLGFLQ-RSSNFQCQKL-LWQLNGRLEY-CLKDRMNFDI-PEEEFDGNQF- 60          70          80          90         100
QKAPAILTIY-EMLQNIFAIF-RQDSSSTGWN-ETIVENLLAN-VYHQINHLKT- 110         120         130         140         150
VLEEKLEKED-FTRGKLMSSL-HLKRYYGRIL-HYLKAKEYSH-CAWTIVRVEI-

160
LRNFYFINRL-TGYLRN<
```

FIG. 3j

Synthetic IFN-β gene

ClaI                                                                              PstI
                                        5                                          10
                MET SER TYR ASN LEU LEU GLY PHE LEU GLN
CGA TAA GCT ATG TCT TAC AAC CTG CTG GGC TTC CTG CAG 15                      20
ARG SER SER ASN PHE GLN CYS GLN LYS LEU LEU TRP GLN
CGT TCT TCT AAC TTC CAA TGC CAG AAA CTG CTG TGG CAA

XmaIII
        25                      30                      35
LEU ASN GLY ARG LEU GLU TYR CYS LEU LYS ASP ARG MET
CTG AAC GGC CGC CTG GAA TAC TGC CTG AAA GAC CGC ATG

PvuII
                41                      45
ASN PHE ASP ILE PRO GLU GLU ILE LYS GLN LEU GLN GLN
AAC TTT GAT ATC CCA GAA GAA ATC AAA CAG CTG CAA CAG 50                      55                      60
PHE GLN LYS GLU ASP ALA ALA LEU THR ILE TYR GLU MET
TTC CAA AAA GAA GAT GCA GCG CTG ACT ATC TAC GAA ATG

NruI                    HinfI
        65                      71              75
LEU GLN ASN ILE PHE ALA ILE PHE ARG GLN ASP SER SER
CTG CAA AAC ATC TTC GCG ATC TTC CGT CAA GAC TCT TCC 80                      85
SER THR GLY TRP ASN GLU THR ILE VAL GLU ASN LEU LEU
TCT ACT GGT TGG AAC GAA ACT ATC GTA GAA AAC CTG CTG AccI
        90                      95              100
ALA ASN VAL TYR HIS GLN ILE ASN HIS LEU LYS THR VAL
GCA AAC GTA TAC CAT CAG ATC AAC CAT CTG AAA ACC GTG SacII
                105                     110
LEU GLU GLU LYS LEU GLU LYS GLU ASP PHE THR ARG GLY
CTG GAA GAG AAA CTG GAA AAA GAA GAC TTC ACC CGC GGT SacI
115                             122             125
LYS LEU MET SER SER LEU HIS LEU LYS ARG TYR TYR GLY
AAA CTG ATG AGC TCC CTG CAT CTG AAA CGC TAC TAT GGT 130                     135                     140
ARG ILE LEU HIS TYR LEU LYS ALA LYS GLU TYR SER HIS
CGT ATC CTG CAT TAC CTG AAA GCT AAA GAA TAC TCT CAC

FIG.3j(CONT'D.)

MstI

```
                    145                         150
     CYS ALA TRP THR ILE VAL ARG VAL GLU ILE LEU ARG ASN
     TGC GCA TGG ACT ATT GTA CGC GTT GAA ATC CTG CGT AAC

BstEII
           155                 160                         166
     PHE TYR PHE ILE ASN ARG LEU THR GLY TYR LEU ARG ASN
     TTC TAC TTC ATC AAC CGC CTG ACT GGT TAC CTG CGT AAC

BamHI

TER
     TAA GGA TCC
```

R<AMSYNLLGFLQRSSNFQCQKLLWQLNGRLEYCLKDRMNFDIPEEIKQLQQF
QKEDAALTIYEMLQNIFAIFRQDSSSTGWNETIVENLLANVYHQINHLKTVLE
EKLEKEDFTRGKLMSSLHLKRYYGRILHYLKAKEYSHCAWTIVRVEILRNFYF
INRLTGYLRN<GS

FIG.3k

IFNX403

IFN-β{β$^{9-56}$→α$_2$$^{7-53}$}{Leu$^{17}$→Cys$^{17}$}

TRIPLE LETTER CODE
(*** REPRESENTS TERMINATOR SEQUENCE)

```
                    5                           10                          15
MET-SER-TYR-ASN-LEU-LEU-GLY-PHE-HIS-SER-LEU-GLY-SER-ARG-ARG-
ATG AGC TAC AAC TTG CTT GGA TTC CAT TCT CTC GGC TCT AGA CGT 20                           25                          30
THR-CYS-MET-LEU-LEU-ALA-GLN-MET-ARG-LYS-ILE-SER-LEU-PHE-SER-
ACC TGT ATG CTG CTC GCT CAG ATG AGA AAG ATA TCC CTG TTC TCT 35                           40                          45
CYS-LEU-LYS-ASP-ARG-HIS-ASP-PHE-GLY-PHE-PRO-GLN-GLU-GLU-PHE-
TGC CTG AAG GAC CGC CAC GAC TTC GGC TTC CCT CAG GAA GAA TTC 50                           55                          60
GLY-ASN-GLN-PHE-GLN-LYS-ALA-GLU-THR-ILE-LEU-THR-ILE-TYR-GLU-
GGC AAT CAG TTT CAG AAA GCT GAA ACG ATT CTG ACC ATC TAT GAG 65                           70                          75
MET-LEU-GLN-ASN-ILE-PHE-ALA-ILE-PHE-ARG-GLN-ASP-SER-SER-SER-
ATG CTC CAG AAC ATC TTT GCT ATT TTC AGA CAA GAT TCA TCT AGC 80                           85                          90
THR-GLY-TRP-ASN-GLU-THR-ILE-VAL-GLU-ASN-LEU-LEU-ALA-ASN-VAL-
ACT GGC TGG AAT GAG ACT ATT GTT GAG AAC CTC CTG GCT AAT GTC 95                          100                         105
TYR-HIS-GLN-ILE-ASN-HIS-LEU-LYS-THR-VAL-LEU-GLU-GLU-LYS-LEU-
TAT CAT CAG ATA AAC CAT CTG AAG ACA GTC CTG GAA GAA AAA CTG 110                          115                         120
GLU-LYS-GLU-ASP-PHE-THR-ARG-GLY-LYS-LEU-MET-SER-SER-LEU-HIS-
GAG AAA GAA GAT TTC ACC AGG GGA AAA CTC ATG AGC AGT CTG CAC 125                          130                         135
LEU-LYS-ARG-TYR-TYR-GLY-ARG-ILE-LEU-HIS-TYR-LEU-LYS-ALA-LYS-
CTG AAA AGA TAT TAT GGG AGG ATT CTG CAT TAC CTG AAG GCC AAG 140                          145                         150
GLU-TYR-SER-HIS-CYS-ALA-TRP-THR-ILE-VAL-ARG-VAL-GLU-ILE-LEU-
GAG TAC AGT CAC TGT GCC TGG ACC ATA GTC AGA GTG GAA ATC CTA 155                          160                         165
ARG-ASN-PHE-TYR-PHE-ILE-ASN-ARG-LEU-THR-GLY-TYR-LEU-ARG-ASN-
AGG AAC TTT TAC TTC ATT AAC AGA CTT ACA GGT TAC CTC CGA AAC
```

***-
TGA

FIG. 3L

IFNX406

IFN-β{β$^{1-56}$→α$_2$$^{1-53}$}{Leu$^{16}$→Cys$^{16}$}

TRIPLE LETTER CODE
(*** REPRESENTS TERMINATOR SEQUENCE)

```
                5                   10                  15
MET-CYS-ASP-LEU-PRO-GLN-THR-HIS-SER-LEU-GLY-SER-ARG-ARG-THR-
ATG TGC GAC TTA CCA CAA ACT CAT TCT CTC GGC TCT AGA CGT ACC 20                  25                  30
CYS-MET-LEU-LEU-ALA-GLN-MET-ARG-LYS-ILE-SER-LEU-PHE-SER-CYS-
TGT ATG CTG CTC GCT CAG ATG AGA AAG ATA TCC CTG TTC TCT TGC 35                  40                  45
LEU-LYS-ASP-ARG-HIS-ASP-PHE-GLY-PHE-PRO-GLN-GLU-GLU-PHE-GLY-
CTG AAG GAC CGC CAC GAC TTC GGC TTC CCT CAG GAA GAA TTC GGC 50                  55                  60
ASN-GLN-PHE-GLN-LYS-ALA-GLU-THR-ILE-LEU-THR-ILE-TYR-GLU-MET-
AAT CAG TTT CAG AAA GCT GAA ACG ATT CTG ACC ATC TAT GAG ATG 65                  70                  75
LEU-GLN-ASN-ILE-PHE-ALA-ILE-PHE-ARG-GLN-ASP-SER-SER-SER-THR-
CTC CAG AAC ATC TTT GCT ATT TTC AGA CAA GAT TCA TCT AGC ACT 80                  85                  90
GLY-TRP-ASN-GLU-THR-ILE-VAL-GLU-ASN-LEU-LEU-ALA-ASN-VAL-TYR-
GGC TGG AAT GAG ACT ATT GTT GAG AAC CTC CTG GCT AAT GTC TAT 95                  100                 105
HIS-GLN-ILE-ASN-HIS-LEU-LYS-THR-VAL-LEU-GLU-GLU-LYS-LEU-GLU-
CAT CAG ATA AAC CAT CTG AAG ACA GTC CTG GAA GAA AAA CTG GAG 110                 115                 120
LYS-GLU-ASP-PHE-THR-ARG-GLY-LYS-LEU-MET-SER-SER-LEU-HIS-LEU-
AAA GAA GAT TTC ACC AGG GGA AAA CTC ATG AGC AGT CTG CAC CTG 125                 130                 135
LYS-ARG-TYR-TYR-GLY-ARG-ILE-LEU-HIS-TYR-LEU-LYS-ALA-LYS-GLU-
AAA AGA TAT TAT GGG AGG ATT CTG CAT TAC CTG AAG GCC AAG GAG 140                 145                 150
TYR-SER-HIS-CYS-ALA-TRP-THR-ILE-VAL-ARG-VAL-GLU-ILE-LEU-ARG-
TAC AGT CAC TGT GCC TGG ACC ATA GTC AGA GTG GAA ATC CTA AGG 155                 160                 165
ASN-PHE-TYR-PHE-ILE-ASN-ARG-LEU-THR-GLY-TYR-LEU-ARG-ASN-***-
AAC TTT TAC TTC ATT AAC AGA CTT ACA GGT TAC CTC CGA AAC TGA
```

FIG. 4

Nucleotide sequence of trp promoter region of IFN-β
expression plasmid pl-24/C

EcoRI                                                                                        HincII       TaqI

GAATTCATTGTCCGACATCATAACGGTTCTGGCAAATATTCTGAAATGAGCTGTTGACAATTAATCATCGAA

−35

HpaI                     (TaqI)
HincII   RsaI            ClaI
               *Transcription initiation
                                        13

CTAGTTAACTAGTACGCAAGTTCACGTAAAAAGGGTATCGATAAGCT.ATG.AGC.TAC.AAC.TTG.CTT.

−10                     S.D.                        Met Ser Tyr Asn Leu Leu
                                                                                    N-terminus mature IFN-β

MODIFIED (1-56) BETA INTERFERONS

BACKGROUND OF THE INVENTION

1. Field of the Invention

This invention describes the use of recombinant DNA technology for the design and synthesis of novel modified interferons. More specifically the invention relates to interferons not known in nature, which are intended for use in viral and neoplastic diseases, and immunosuppressed and immunodeficient conditions.

2. Description of the Prior Art

The interferons are a class of proteins that occur in vertebrates and act as biological regulators or cell function which include increasing resistance to pathogens, limiting cell growth and modulating the immune system. The most studied property of the interferons is their ability to convert cells into an "antiviral state" during which they are more resistant to virus replication (Lengyel, Annual Review of Biochemistry, 51, 251, 1982). In addition to conferring antiviral resistance to target cells, interferon (IFNs) have antiproliferative (antigrowth) properties (Stewart, 1979, The Interferon System, Springer, Berlin). It has clearly been shown that interferons produced naturally act as antiviral and antiproliferative agents (Gresser et al, Biochim. Biophys. Acta, 516, 231, 1978; J. Exp. Med., 144, 1316, 1976).

The IFNs, by virtue of their antigenic, biological and physico-chemical properties, may be divided into three classes: type I, IFN-α("leucocyte") and IFN-β ("fibroblast"); and type II, IFN-γ ("immune") (Stewart et al, Nature, 286, 110, 1980). Both genomic DNA cDNA clones of type I and type II IFNs have been isolated and sequenced, and the potential protein sequences deduced (e.g. Pestka, Arch. Biochem. Biophys., 221, 1, 1983). While in man only one IFN-β and IFN-γ gene are known, human IFN-α is specified by a multigene family comprising at least 20 genes. The classification of IFN-β and IFN-α as type I interferons is in part determined by their significant degree of homology, >23% at the protein level (Taniguchi et al, Nature, 285, 547, 1980).

While the mechanism of action of interferons is not completely understood, certain physiological or enzymatic activities respond to the presence of the interferons. These activities include RNA and protein synthesis. Among the enzymes induced by interferons is (2'-5') (A)n synthetase generates 2'-5' linked oligonucleotides, and these in turn activate a latent endoribonuclease, RNAse L, which cleaves single-stranded RNA, such as messenger RNA (mRNA) and ribosomal RNA (rRNA). Also induced by IFNs is a protein kinase that phosphorylates at least one peptide chain initiation factor and this inhibits protein synthesis (Lengvel, ibid, p 253). IFNs have been shown to be negative growth regulators for cells by regulation of the (2'-5') An synthetase activity (Creasey et al, Mol and Cell Biol., 3, 780, 1983). IFN-β was indirectly shown to be involved in the normal regulation of the cell cycle in the absence of inducers through the use of anti-IFN-β antibodies. Similarly, IFNs have been shown in have a role in differentiation (Dolei et al, J. Gen. Virol., 46, 227, 1980) and in immunomodulation (Gresser, Cell Immunol, 34.406 1977). Finally IFNs may alter the methylation pattern of mRNAs and alter the proportion of fatty acids in membrane phospholipids thereby changing the rigidity of cell membranes.

These and other mechanism may respond to interferon-like molecules in varying degrees depending on the structure of the interferon-like polypeptide Preliminary evidence (UK Pat. GB No. 2 090 258A) suggests that members of the multigene IFN-α family vary in the extent and specificity of their antiviral activity (Pestka ibid). For example combination of IFN-αA with IFN-αD resulted in "hybrid" genes which show antiviral properties that are distinct from either parent molecule (Weck et al. Nucl. Acids Res., 9. 6153, 1981; De La Maza et al, J. IFN Res., 3, 359, 1983; Fish et al. Biochem. Biophys. Res. Commun., 112, 537, 1983; Weck et al. Infect. Immun., 35, 660, 1982) However hybrid human IFNs with significantly increased human cell activity/specificity have not yet been developed. One Patent has been published describing IFN-β/αhybrids (PCT/US83/00077) This patent describes three examples none of which have significantly improved activity. The three examples were constructed using two naturally occurring restriction sites. The resulting hybrid interferons were (1) alpha 1 (1-73)-beta (74-166), (2) beta (1-73)-alpha 1 (74-166), and (3) alpha 61A (1-41)-beta (43-166). These three examples differ structurally from the examples of the present invention These three examples were based upon the accidental location of two restriction sites and not upon the intentionally designed DNA and amino acid sequences of the present invention.

It is envisioned that a modified interferon will display a new advantageous phenotype The design and synthesis of new interferon-like polypeptides composed of portions of IFN-β and other amino acid sequences is advantageous for the following reasons:

1. New IFNs can be created which show a greater antiproliferative to antiviral activity (and vice versa) resulting from the selective activation of only some of the normal interferon-induced biochemical pathways.
2. The affinity of hybrid or modified IFNs for cell surface receptors can differ from that of naturally occurring interferons. This will allow selective or differential targeting of interferons to a particular cell type or increased affinity for the receptor-leading to increased potency against a particular virus disease or malignancy.
3. It will be possible to design novel IFNs which have an increased therapeutic index thus excluding some of the undesirable side effects of natural IFNs which limit their use (Powledge, TM Biotechnology, 2, 214, March 1984).
4. Novel IFNs can include in the design structures which allow increased stability to proteolytic breakdown during microbial synthesis.
5. Novel IFNs can be designed to increase their solubility or stability in vivo. and prevent non-specific hydrophobic interactions with cells and tissues.
6. Novel IFNs can be designed which are more readily recovered from the microbial supernatant or extract and more easily purified.

Additional Relevant Patent Applications

UK No. GB2 116 566A—Animal interferons and processes for their production
U.S. Pat. No. 4,414,150—Hybrid human luekocyte interferons UK No. GB 2 068 970A—Recombinant DNA technique for the Preparation of a protein resembling human interferon

SUMMARY OF THE INVENTION

Recombinant DNA technologies were successfully applied to produce modified beta interferon-like polypeptides nucleic acids (either DNA or RNA) which code for these modified beta interferons plasmids containing the DNA coding for the modified beta interferons and procedures for the synthesis of these modified beta interferons. Each of the amino acids 1-56 of human beta interferon may individually be replaced by any other amino acid. This replacement may be accomplished in groups of three to fifty-six amino acids. One preferred embodiment is the replacement of each amino acid from 2 to 7 and 9 to 56 of human beta interferon by another amino acid. Another preferred embodiment is the replacement of each beta interferon amino acid from 9 to 56 by four to forty-seven other amino acids. The beta interferon amino acids 2 to 7 and 9 to 56 may be replaced by corresponding sequential human alpha interferon amino acids Among the alpha interferons are alpha 1, alpha 2 and alpha H The alpha and beta interferons from any mammal may be used, including but not limited to humans or other primates, horses, cattle, sheep, rabbits, rats and mice. In one embodiment of the invention the cysteine 17 or methionine 31 in human beta interferon may optionally be replaced by serine 17 (or leucine 17) and/or lysine 31. In some examples, e.g. IFNX410 (Chart 3d) the cysteine or leucine or serine at position 17 is renumbered as position 16 because the inserted amino acids upstream of position 17 contain one less amino acid. Yet another embodiment of the invention discloses the use of the modified beta interferons where in one or more of the antiviral cell growth regulatory or immunomodulatory activities is substantially changed from that of the unmodified beta interferon. Particularly preferred embodiments are the amino acid sequences of IFNX402. 403 404, 406, 407, 408, 409, 410, 415, 419, and 420. Yet another preferred embodiment of the invention is DNA or RNA sequences which code for the synthesis of IFNX402, 403, 404, 406, 407, 408, 409, 410, 415, 419, or 420. Yet another embodiment of the invention is a pharmaceutical composition containing an effective amount of TFNX402, 403, 404, 406, 407, 408, 408, 409, 410, 415, 419, 420. A final embodiment of the invention is the use of pharmaceutical compositions containing the modified beta interferons in a method of treating viral infections, regulating cell growth or regulating the immune system.

It was reported that the change of amino acid residue 17 from cysteine to serine markedly increased the specific antiviral activity of IFN-$\beta$ produced in *E.coli* (TNO Interferon meeting, Rotterdam, April 1983). In the present invention this result is not confirmed, and the alterations in biological activity demonstrated by some of the novel IFNs (shown in Tables 1-16) are therefore not due to the Ser[17]. Other amino acids may be present at residue 17 (or residue 16, e.g. Chart 3d) such as cysteine, leucine or alanine. In the present disclosure, the amino acid at residue 17 is either cysteine, serine or leucine.

Novel, modified IFNs with increased biological activity are disclosed in the present invention which may be more effective in the treatment of viral or neoplastic diseases or immunosuppressed or immunodeficient conditions. Novel modified IFNs are disclosed which have substantially lost one or other of the activities measurable in vitro (e.g. antiviral, antiproliferative or immunomodulatory).

An increased target cell specificity or an increase in IFN activity can result in an improved therapeutic index This should exclude some of the side effects caused by the use in humans of naturally occurring IFNs.

This invention relates to the production in sufficient amounts of novel, highly active, and/or highly specific interferon-like molecules suitable for the prophylactic or therapeutic treatment of humans—notably for viral infections malignancies and immunosuppressed or immunodeficient conditions.

BRIEF DESCRIPTION OF THE CHARTS AND TABLES

FIG. 2(a to g) shows the ligated oligonucleotides used in the construction of the novel modified IFN genes FIG. 3 (a to j) shows the complete nucleotide sequences of the novel, modified IFN genes and the encoded amino acid sequences FIG. 3K shows the nucleotide sequence and amino acid sequence of modified interferon IFNX403.

FIG. 3L shows the nucleotide sequence and encoded amino acid sequence of modified interferon IFNX406.

FIG. 4 shows the nucleotide sequence of the trp promoter used to initiate transcription of the novel, modified IFN genes Table 1 compares expression, antiviral and antiproliferative activities in bacterial extracts for some novel, modified IFNs Table 2 compares antiviral activities of IFN-$\beta$, IFNX805 and IFNX415 in 3 different cell lines.

Table 3 compares antiproliferative activities of IFNX805 and IFNX415 in 3 different cell lines.

Table 4 compares the ability of purified IFN-$\beta$, IFNX805 and IFNX415 to stimulate Antibody-Dependent Cellular Cytotoxicity (ADCC).

DESCRIPTION OF THE PREFERRED EMBODIMENTS

Introduction

Figure 1:
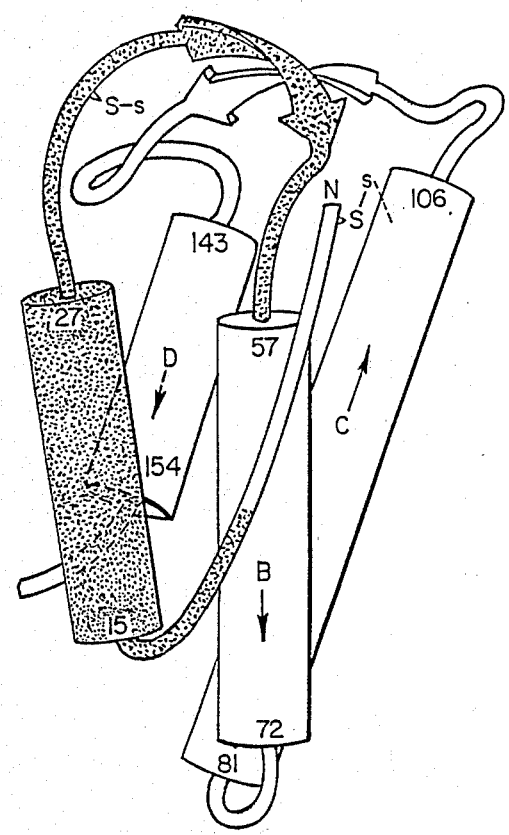
FIG. 1 shows the Sternberg-Cohen 3D model of $\alpha_1$ and $\beta$ interferons.
Figure 1:
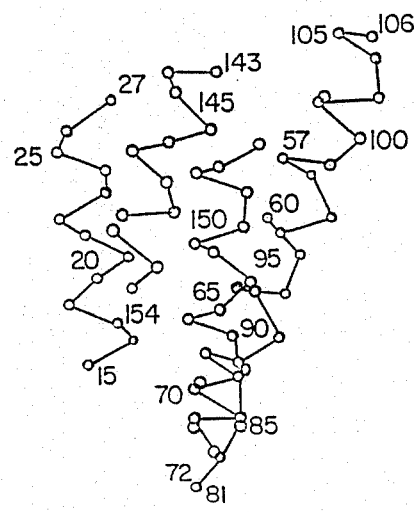
Figure 1:
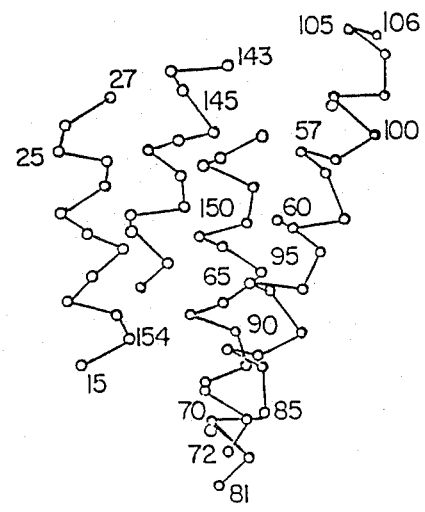

The IFN-$\beta$ gene is a unique gene but shows some significant homologies to the multigenic IFN-$\alpha$ family (Rubinstein, Biochim. Biophys. Acta, 695, 5, 1982). Sternberg and Cohen (Int. J. Biol. Macromol., 4, 137, 1982) have proposed a similar secondary structure for IFN-$\beta$ and IFN-$\alpha_1$. Structure prediction studies suggest four $\alpha$-helices which can be "packed" into a right-handed bundle (FIG. 1) similar to that observed in several unrelated protein structures as determined by X-ray crystallography. The design of some of the modified interferons described herein is derived from our interpretation of the Sternberg/Cohen model. Since IFNs $\beta$ and $\alpha$ are believed to bind to the same receptor at the cell surface it is possible to introduce variability into IFN-$\beta$ by replacing specific areas with IFN-$\alpha$ segments or any other amino acid sequence. The construction of these interferons has resulted in novel, hybrid interferons with altered biological properties. All these interferons were active to some degree suggesting a large measure of variability in the nature of the inserted amino acid sequence which would give rise to an active molecule.

In this invention each amino acid in the 1 to 56 region can be replaced by any other naturally occurring amino acid. The naturally occurring amino acids and their nomenclature are: alanine (Ala or A); valine (Val or V); leucine (Leu or L); isoleucine (Ile or I); proline (Pro or P); phenylalanine (phe or F); tryptophan (Trp or W); methionine (Met or M); glycine (Gly or G); serine (Ser or S); threonine (Thr or T); cysteine (Cys or C); tryosine (Tyr or Y); asparagine (Asn or N); glutamine (Glu or Q); aspartic acid (Asp or D); glutamic acid (Glu or E); lysine (Lys or K); arginine (Arg or R); and histidine (His or H).

Accordingly, the field of the present invention is the design, synthesis and characterization of interferon-like molecules related to IFN-$\beta$ which may have IFN-$\beta$ amino acid sequences replaced with any other amino acid sequence, unrelated protein sequence, or sequences similar to those of IFN-$\alpha$s, -$\beta$ or -$\gamma$ found in mammals and other vertebrates.

Though binding of hybrid IFN-$\alpha$'s ($\alpha_1$ and $\alpha_2$ in Streuli et al. Proc. Natl. Acad. Sci. USA, 78; 2848; 1981); an attempt was made to analyse the number and nature of idiotypes involved in the receptor binding site of IFN-$\alpha$'s. Two sites were proposed as constituting the binding site, one in the amino-terminal half and the other in the carboxy-terminal half of IFN-$\alpha$. The two major regions of partial homology between IFN-$\alpha$'s and IFN-$\beta$ occur between amino acid residues 28–80 and 115–151 which may well correspond to the above mentioned idiotypes. Evidence that the 28–80 region may be important in receptor binding come from the finding that polyclonal antibodies raised against a synthetic peptide composed of IFN-$\alpha_2$ amino acids 24–81, bind to IFN-$\alpha_2$ and prevent it interacting with its cell receptor (Dreiding TNO Interferon Meeting Rotterdam 1983). The modified interferons of this invention, such as IFNX402 (IFN-$\beta[\beta(9-56)]$-$[\alpha_1(7-54)]$) display dramatically reduced human cell antiviral and natural killer cell activities relative to antiproliferative activity. Other examples of novel interferons derived from IFN-$\beta$ having altered amino acids between IFN-$\beta$ residues ~9 and ~56 were among those synthesized. IFN-$\beta[\beta(9-56)\rightarrow\alpha_1(7-54)]$ denotes that amino acid residues 9–56 inclusive of IFN-$\beta$ are replaced by residues 7–54 of IFN-$\alpha_1$. These examples illustrate the invention and are not intended to limit the scope of the invention in any way. Below are described techniques used in the design chemical synthesis and insertion of DNA fragments in the 1–56 region of the human IFN-$\beta$ gene The resultant novel, modified IFNs are hereafter described as group II IFNs. Decreased antiviral or increased antiproliferative activity are among the altered properties shown by some of the group II novel IFNs with amino acid replacements in the 1–56 region. The techniques described will be familiar to anyone skilled in the art [e.g. see also Molecular Cloning: A Laboratory Manual, eds Maniatis et al, Cold Spring Harbor Laboratories].

Design of the synthetic gene fragments

The nucleotide sequences of each synthetic DNA fragment (Charts 2a–2e) were designed utilizing the following criteria.
1. Codon utilization (where it deviates from IFN-$\beta$ gene sequence) was optimized for expression in E.coli. Natural IFN-$\beta$ gene sequences were used as far as possible in order to obtain levels of expression of novel IFNs as high as that of IFN-$\beta$ from plasmid pGC10 (see Table 1). pGC10 (~4,440 bp) expresses the natural IFN-$\beta$ gene at a high level and is identical to p1/24 (Searle Patent GB 2 068 970A, hereby incorporated by reference) except for the ribosome binding site sequence shown in Chart 4 and the deletion of the ~546 bp BglII-BamHI fragment.
2. Sequences which might anneal to each other in the assembly of the chemically synthesized fragment (Chart 2) were not included in the design (within the limits allowed by the redundancy in the genetic code).

Chemical Synthesis of Gene Fragments

Oligodeoxyribonucleotides were synthesized by the phosphoramidite method (M. H. Caruthers in "chemical and Enzymatic synthesis of Gene Fragments" ed. H. G. Gasen and A Lang, Verlag Chemie, 1982. p 71) on controlled pore glass (H. Koster et al; Tetrahedron, 40, 103, 1984). Fully protected 2'-deoxyribonucleotide 3'-phosphoramidites were synthesized from the protected deoxyribonucleotide and chloro-N,N-(diisopropylamino)methoxyphosphine (L. J. McBride and M H Caruthers, Tetrahedron Lett., 24, 245, 1983 and S. A. Adams et al, J. Amer. Chem. Soc., 105, 661, 1983). Controlled pore glass supports were synthesized as described (F. Chow et al, Nuc. Acids Res., 1981, 9, 2807) giving 30–50 $\mu$mol deoxynucleoside per gram.

The functionalised controlled pore glass (50 mg) was treated in a sintered glass funnel at ambient temperature sequentially with:
1. dichloromethane (3 ml 10 s)
2. 3% ($^v$/v) dichloroacetic acid in dichloromethane (2 ml 120 s)
3. dichloromethane (3 ml 10 s)
4. anhydrous acetonitrile (3 ml 10 s)
5. phosphoramidite monomer (0.06M)/tetrazole (0.23M) in anhydrous acetonitrile (1 ml. 120 s)
6. acetonitrile (3 ml. 10 s)
7. dimethylaminopyridine (0.07M) in acetic anhydride/2-6-lutidine/acetonitrile (1/2/6$^v$/v) (1 ml. 60 s)
8. acetonitrile (3 ml 10 s)
9. iodine (0.2M) in 2.6-lutidine/tetrahydrofuran/water (1/2/2$^v$/v) (1 ml. 30 s)
10. acetonitrile (3 ml. 10 s)

The cycle was repeated with the appropriate phosphoramidite monomer until the immunogenetic chain was complete. The coupling efficiency of each cycle was monitored by spectrophotometric assay of the liberated dimethoxytrityl alcohol in 10% ($^w$/v) trichloroacetic acid/dichloromethane at 504 nm. After completion of the synthesis the protecting groups were removed and the oligomer cleaved from the support by sequential treatment with 3% ($^v$/v) dichloroacetic acid/dichloromethane 9120 s). thiophenol/triethylamine/dioxan (1/1/2 $^v$/v) (1 h) and concentrated ammonia at 70° C. (4 h). The deprotected oligonucleotides were purified either by HPLC on a Partisil 10 SAX column using a gradient from 1M to 4M triethylammonium acetate pH 4.9 at 50° C. or by electrophoresis on a denaturing 15% polyacrylamide gel (pH 8.3).

Ligation of Oligonucleotide Blocks 500 pmole aliquots of the oligonucleotides were phosphorylated with 1 unit of T4 induced polynucleotide kinase in 20 μl of a solution containing 1000 Ci/pmole [$^{32}$p]γ-ATP (2.5 Ci/mMole), 100 μM spermidine. 20 mM DTT 10 mM MgCl$_2$. 50 mM Tris-HCl (pH 9.0) and 0.1 mM EDTA for 60 minutes at 37° C. The mixtures were then lyophilized and each oligonucleotide purified in a denaturing 15% polyacrylamide gel (pH 8.3). After elution from the gel, the recovery was determined by counting the radioactivity.

Blocks (length 30–50 bases) were assembled by combining 25 pmole of each phosphorylated component with equimolar amounts of the unphosphorylated oligomers from the complementary strand. The mixtures were lyophilized and then taken up in 15 μl water and 2 μl 10×ligase buffer (500 mM Tris-HCl pH 7.6, 100 mM MgCl$_2$). The blocks were annealed at 100° C. for 2 minutes then slowly cooled to room temperature (20° C.). 2 μl 200 mM DTT and 0.5 μl 10 mM ATP were added to give final concentrations of 20 mM DTT and 250 μM ATP in 20 μl. 1.25 units of T4 DNA ligase were also added. After 18 hours at 20° C. the products were purified in a 15% polyacrylamide gel under denaturing conditions.

Two duplex blocks were then constructed from the single-stranded pieces. (These were 150 base pairs and 75 base pairs). 1.5 pmole of each block were taken and the mixtures lyophilized. Annealing was carried out in 15 μl water and 2 μl 10×ligase buffer at 100° C. for 2 minutes then slowly cooled to 10° C. 2 μl 200 mM DTT 0.5 μl 10 mM ATP and 1.25 units T4 DNA ligase were added. The reaction was left at 10° C. for 18 hours. The products were then purified in a 10% native polyacrylamide gel.

The final product was assembled by combining 0.4 pmole of the two duplexes. The mixture was lyophilized and then taken up in 15 μl water and 2 μl 10×ligase buffer. It was annealed at 50° C. for 2 minutes and then slowly cooled to 10° C. 2 μl 20 mM DTT 0.5 μl 10 mM ATP and 1.25 units ligase were then added and the reaction left at 10° C. for 18 hours. The final product was purified in a 5% native polyacrylamide gel. After elution and ethanol precipitation the product was taken up in 10 μl water. 0.5 μl were removed for counting to calculate the recovery. 2 μl 10×ligase buffer, 2 μl 200 mM DTT, 2 μl 1 mM spermidine, 1 μl 10 mM ATP, 3 μl water and 0.5 units kinase were added to the rest (total volume 20 μl) The reaction was left at 37° C. for 1 hour and stopped by heating at 90° C. for 2 minutes. The final product was ethanol precipitated.

Construction of plasmids expressing novel modified interferons

This section lists and identifies the vectors employed in the cloning of the synthetic DNA fragments (Chart 2) into the IFN-β coding region. the restriction enzyme sites* used for the insertion, and the rationale for the construction. The positions of these sites* are shown relative to the complete coding nucleotide sequences of the group II novel IFN genes (Chart 3). The IFN-β (or novel IFN) coding region is shown as a heavy line and would be translated from left to right. The vector sequences between the BglII (or BamHI) site and the EcoRI site are the same as those in pAT153 (equivalent to pBR322 with a 705 bp HaeII fragment deleted—nucleotides 1,646–2,351 on the map). A vector denoted by "m" instead of "p" refers to M13 mp8 sequences between the EcoRI and BamHI sites. The E.coli trp promoter (Chart 4) lies between the EcoRI site and ClaI site (or equivalent position in IFNX407, X408 and X409).

EXAMPLE 1

IFNX407 IFN-β[β$^{9-56}$→α$_1$$^{7-54}$]

This is IFNX402 with a change from Cys$^{17}$ to Leu$^{17}$ and was designed to determine the effect of residue 17 on antiviral and antiproliferative activity.

Starting vector: pMN39-1. pMN39-1 is identical to p1/24 (UK Patent—Application GB No. 2 068 970A) except that the ~546 bp BglII-BamHI fragment is deleted.

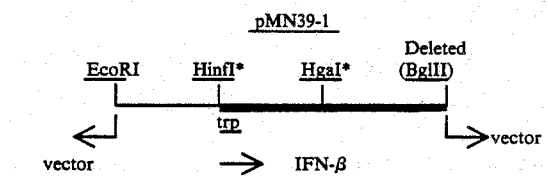

A synthetic olignonucleotide (Chart 2a) was inserted between the HinfI* and HgaI* sites to give the nucleotide sequence shown in FIG. 3a. INFX407 is expressed from plasmid pJA29.

EXAMPLE 2

IFNX408 IFN-β[β$^{44-56}$→α$_1$$^{42-54}$][Cys$^{17}$→Ser]

This is derived from IFNX404 and was designed to determine the effect of the change of residue 17 from Cys to Ser (IFN-β with Ser$^{17}$ was first disclosed by Cetus Corp., TNO Interferon Meeting, Rotterdam, April 1983).

Starting vector: pXX404. pXX404 is similar to p1/24 (UK Patent Filing Application GB No. 2 068 970A), except that the IFN-β amino acid residues 44-56 are replaced by IFN-α$_1$ residues 42-54.

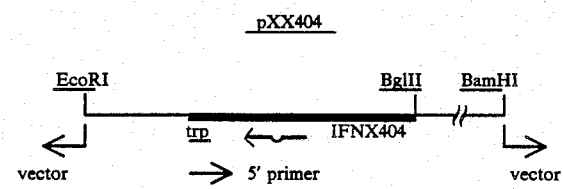

The Cys$^{17}$→Ser change to pXX404 was accomplished by olignonucleotide-directed (or site-directed) mutagenesis (Zoller and Smith, Nucl. Acids Res., 10, 6487, 1982) An EcoRI-BamHI (~1,176 bp) fragment was subcloned in M13 mp 8 for mutagenesis using the primer 5'-CTGACTCTGAAAATTG-3' to give M13 recombinant, mJA8. Clones with the codon 17 sequence 5'-AGT-3' (Ser) were isolated (mJA9) and an EcoRI-BglII fragment subcloned in the EcoRI-BamHI vector fragment of pXX404 to give IFNX408 expression plasmid pJA27 (Chart 3b).

EXAMPLE 3

IFNX409 IFN-β[β$^{42-56}$→α$_1$$^{40-54}$][Cys$^{17}$→Ser]

IFNX409 is an analogue of IFNX408 (and IFNX404) and was designed to replace the Glu at amino acid residue 42 with Gln to test the effect of changing the predicted secondary structure, since the Glu-Glu-Glu sequence (at residues 42-44) was considered unfavourable.

Starting vector: mJA9 (see above). This phage M13 vector contains the entire coding sequence of IFNX408 on an EcoRI-BamHI fragment.

```
                        mJA9
    EcoRI                     BglII    BamHI
    ├──────────────────────────┼────────┤
    ←    trp     ←                      //
    M13        → 5' primer IFNX404     M13
    vector                             vector
```

The Glu$^{42}$→Gln change to mJA9 was accomplished by oligonucleotide-directed mutagenesis as above using the primer 5'-AAACTCTTCTTGAGGATGTC-3', with the modification described by Norris et al, Nucl. Acids Res., 11. 5103 1983. Clones with the codon 42 Sequence 5'-CAA-3' (Gln) were isolated and an EcoRI-BqlII ~620 bp fragment subcloned in the EcoRI-BamHI vector fragment of pXX404 to give pJA31, the plasmid expressing IFNX409 (Chart 3c).

EXAMPLE 4

IFNX410 IFN-$\beta[\beta^{2-7}\rightarrow\alpha_2^{1-5}][\beta^{9-56}\rightarrow\alpha_1^{7-54}]$ This modified, novel IFN was constructed to investigate the additive, synergistic or other effect of combining in one molecule sequences from two different IFN-$\alpha$'s. IFNX410 is related to IFNX402.

Starting vector: pMN47. This vector contains an entirely synthetic IFN-$\beta$ gene (Chart 3j) inserted between the ClaI and BamHI sites of p1/24C (p1/24C is identical to p1/24 except for the underlined sequences in Chart 4).

```
                    pMN47
    EcoRI     ClaI*    NruI*    BamHI
    ├──────────┼────────┼────────┤
    ←    trp         IFN-β
    vector     →              vector
```

A synthetic oligonulceotide (Chart 2b) was inserted between the ClaI* and NruI* sites to give the nucleotide sequence shown in Chart 3d. IFNX410 is expressed from plasmid pAS213.

EXAMPLE 5

IFNX415
IFN-$\beta[\beta^{28-46}\rightarrow\alpha_1^{28-46}][Cys^{17}\rightarrow Ser][Met^{31}\rightarrow Lys]$ This novel, nodified IFN was designed to test the generality and extent of substitutions in the 9-56 region of IFN-$\beta$ causing decreased antiviral activity, and to enhance or depress other IFN activities.

Starting vector: pAP4. pAP4 expresses IFN-$\beta$ and is identical to pGC10 except that the serines at amino acid residues 74 and 75 are coded by TCC and TCG, respectively. These serine codons were changed from TCA and TCT in order to introduce an unique XhoI site to facilitate the insertion of synthetic DNA. This was accomplished by oligonucelotide-directed mutagenesis (Zoller and Smith, Nucl. Acids Res., 10, 6487, 1982) using the mismatch primer: 5'-CAGTGCTCGAG-GAATCTTGTC-3'.

```
                   pAP4
    EcoRI    ClaI*   XhoI*    (BglII) deleted
    ├─────────┼───────┼───────────────┤
    ←    trp         IFN-β
    vector    →                    vector
```

A synthetic oligonucleotide (Chart 2c) was inserted between the ClaI* and XhoT* sites of pAP4 to give the nucleotide sequence shown in Chart 3e. IFNX415 is expressed from plasmid pAP7.

EXAMPLE 6

IFNX402 IFN-$\beta[\beta^{9-56}\rightarrow\alpha_1^{7-54}][Leu^{17}\rightarrow Cys^{17}]$ This novel, modified IFN was designed to examine the effect of substituting a region from IFN-$\alpha_1$ into IFN-$\beta$ on relative antiviral antiproliferative and immunostimulating activities.

Starting vector: p1/24, as above

It contains the mature, natural human IFN-$\beta$ gene which is expressed under trp promoter control.

```
                       p1/24
    EcoRI   HinfI*   HgaI*   BglII      BamHI
    ├─────────┼───────┼───────┼──────//───┤
    ←              IFN-β
    vector    trp                     vector
              →
            promoter
```

A synthetic oligonucleotide (Chart 2d) was inserted between the HinfI* and HgaI* sites of p1/24 to give the nucleotide sequence shown in Chart 3f. IFNX402 is expressed from plasmid pXX402. The ~546 bp BglII-BamHI fragment is then deleted to obtain high level expression.

EXAMPLE 7

IFNX419 IFN-$\beta[\beta^{9-42}\rightarrow\alpha_1^{7-40}]$

This novel, modified IFN was designed to test the generality and extent of substitutions in the 9-56 region of IFN-$\beta$ causing decreased antiviral activity and to enhance other IFN activities. The positioning of the substitution reflects the difference between IFNX402 and IFNX404.

Starting vector: pGC10

```
                   pGC10φ
                                      deleted
    EcoRI    ClaI*    PvuII*         (BglII)
    ├─────────┼────────┼────────────────┤
    ←              IFN-β
    vector    trp                    vector
              →
```

A synthetic oligonucleotide (Chart 2e) was ligated between the ClaI* and PvuII* sites of pGC10 to give the nucleotide sequence shown in Chart 3g. IFNX419 is expressed from plasmid pAP6.

EXAMPLE 8

IFNX420 IFN-$\beta[\beta^{21\text{-}42}\rightarrow\alpha_1^{19\text{-}40}][\text{Cys}^{17}\rightarrow\text{Ser}]$ The rationale for construction was the same as for IFNX415; the changed amino acid sequence was a subset of the changed amino acid sequence in IFNX419($\alpha_1$7-40). A synthetic oligonucleotide (Chart 2f) was ligated between the ClaI* and PvuII* sites of pMN47 to give the nucleotide sequence shown in Chart 3h. IFNX420 is expressed from plasmid pNW25.

EXAMPLE 9

IFNX404 IFN-$\beta[\beta^{44\text{-}56}\rightarrow\alpha_1^{42\text{-}54}]$

This novel, modified IFN was designed to examine the effect of substituting a region from IFN-$\alpha_1$ into IFN-$\beta$ on relative antiviral, antiproliferative and immunostimulating activities.

Starting vector: p1/24. as above

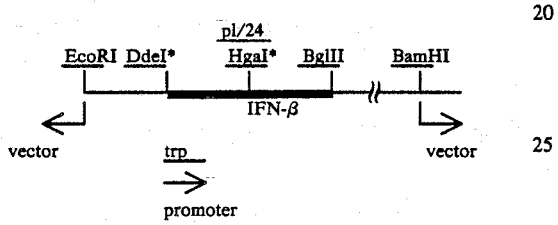

A synthetic oligonucleotide (Chart 2g) was inserted between the DdeI* and HgaI* sites of p1/24 to give the nucleotide sequence shown in Chart 3i. IFNX404 is expressed from plasmid pXX404. The ~546 bp BglII-BamHI fragment is then deleted to obtain high level expression.

EXPRESSION OF NOVEL, MODIFIED IFNS IN *ESCHERICHIA COLI*

All the above mentioned plasmids were grown in *E.coli* HB101 in the presence of a low level of tryptophan to an OD$_{600}$ of 0.5, then induced for IFN synthesis. The medium (200 ml) contained: M9 salts, 0.5% glucose, 0.1 mM CaCl$_2$. 0.5% Casamino acids. 1 mM MgSO$_4$, 0.1 mg/ml vitamin B$_1$, 2.5 $\mu$g/ml tryptophan and 100 $\mu$g/ml carbenecillin.

200 ml of medium was inoculated with 2-4 ml of an overnight culture of each clone (in the host *E.coli* HB101) grown in the above medium except for the presence of 42.5 $\mu$g/ml tryptophan and grown at 37° C. with vigorous aeration. At OD$_{600}$ of 0.5, indole acrylic acid the inducer of the *E.coli* trp promoeter and therefore also of IFN synthesis. was added to 20 $\mu$g/ml. At 4-5 hours after induction 16 ml of culture was withdrawn (OD$_{600}$=0.75-1.2 range) and split as follows: (1) 1 ml was for estimation of total "solubilized" IFN antiviral or antiproliferative activity (the activity regained after a denaturation/renaturation cycle); and (2) 1 ml was for display of the total accumulated *E.coli* proteins plus IFN in a polyacrylamide gel.

(a) Estimation of TOTAL "solubilized" IFN antiviral activity

For recovery of TOTAL "solubilized" IFN antiviral activity. the pellets were vortexed in 20 $\mu$l "lysis buffer" per 0.1 OD$_{600}$ per ml of culture. ("Lysis buffer" is 5M urea, 30 mM NaCl, 50 mM Tris-HCl pH7.5, 1% SDS, 1% 2-mercaptoethanol. 1% HSA). The mixture was heated for 2-3 min. at 90° C., frozen at -70° C. for 15 min., thawed and centrifuged at 17K rpm for 20 min. The supernatant was diluted in 1 log steps to 1:10$^5$ and appropriate dilutions immediately assayed for IFN antiviral activity by monitoring the protection conferred on Vero cells against the cytopathic effect (cpe) of EMC virus in an in vitro micro-plate assay system (e.g. see Dahl and Degre, Acta. Path. Microbiol. Scan., 1380, 863, 1972). The diluent was 50 mM Tris-HCl pH7.5. 30 mM NaCl 1% human serum albumin (HSA).

(b) Polyacrylamide gel electrophoresis of total polypeptides

Cells from 1 ml of culture were mixed with 10 $\mu$l per 0.1 OD$_{600}$ per ml of final sample buffer: 5M urea, 1% SDS, 1% 2-mercaptoethanol, 50 mM Tris-HCl pH7.5, 30 mM NaCl and 0.05% bromophenol blue. The mixture was heated at 90° C. for 5 min., centrifuged for 10 min. and 5-7 $\mu$l loaded on a 15% acrylamide/0.4% bisacrylamide "Laemmli" gel. Electrophoresis was at 70 V for 18 hours. The gel was fixed and stained with Coomassie brilliant blue, then dried and photographed.

Purification and biological properties of IFNX407, X408 and X415

One liter culture was induced and grown to OD$_{600}$ 1-2 as described above. The cell pellet was resuspended in 30 ml 50 mM Tris-HCl pH8.0 and sonicated on ice. 4×1 min at 100 W and then centrifuged for 1 hr at 15K rpm. 30 ml boiling extraction solution (50 mM Tris-HCl pH8.0, 50 mM DTT and 1-2% SDS) was added, mixed and the solution was sonicated. The solution was then boiled for 5 min., centrifuged for 1 hr at 15K rpm. and to the supernatant was added (NH$_4$)$_2$SO$_4$ to 40% saturation. After 15 min. the precipitate was collected by centrifugation at 10K rpm for 20 min. The pellet was redissolved by adding 5 ml warm 50 mM Tris-HCl pH8.0. Following a 15K rpm spin for 1 hr. the solution was re-reduced in 50 mM DTT by boiling for 5 min.

The IFNs were fractionated on a 2.35 cm×70 cm column of LKB AcA44 in 0.1% SDS, 50 mM Tris-HCl pH8.0. and the peak fractions containing 1-2 mg IFN were pooled.

To remove SDS and deplete pyrogens, either (a) the protein was acetone precipitated and redissolved in 50% formic acid, 10% isopropyl alcohol (solvent A); or (b) 6 parts formic acid and 1 part isopropyl alcohol were premixed and added to 3 parts sample. The mixture was applied to C-18 Sep-Pak TM (capacity greater than 3 mg) or to a C-18 Bond Elut (Anachem). The columns were first washed with solvent A (2-4 ml) and the IFN eluted with 50% formic acid 50% isopropyl alcohol.

The eluted IFN was dialysed against water to remove formate and then into GuHCl (6M), 100 mM Tris-HCl pH8.0. To renature the IFN, the sample was reduced in 10 mM DTT at 100° C. then diluted 100-fold into 100 mM Tris-HCl pH8.0, 200 mM KCl. 1 mM EDTA and either 0.1% Tween-20 or 1% HSA. Protein was estimated prior to biological assay.

Antiviral assays of purified, modified interferons

A single virus (encephalomyocarditis—EMC) was used to determine antiviral activity in primate cells. Determinations were made with a virus cytopathic effect (cpe) assay following challenge of cells of Monkey (Vero) and human (Chang conjunctiva and Searle 17/1 fibroblast) origin (Dahl and Degre, ibid.).

Antiproliferative assays of purified novel interferons

Antiproliferative activity was assessed by the ability of the IFN to inhibit the replication of three human cell lines (Horoszewicz et al. Science, 206, 1091, 1979)—Daudi (lymphoblastoid), HEP-2 (carcinoma) and RD (rhabdomyosarcoma). Daudi cells (in log phase) were cultured for 6 days in 96 well plates in the presence of various dilutions of interferon. The phenol red indicator in the medium changes from red to yellow (more acid) with progressive cell growth. Liquid paraffin was added to prevent pH change on exposure to the atmosphere and the pH change in the medium measured colorimetrically on a Dynatech plate reader. Interferon inhibition of cell growth is reflected by a corresponding reduction in the colour change HEP-2 and RD in log growth were cultured for 3 days in 96 well plates in the presence of interferon. The cells were then fixed with 0.25% glutaraldehyde and stained with methylene blue. After extraction into ethanol the colour intensity was measured on a Dynatech plate reader. Once again colour intensity can be related proportionally to cell growth. In vitro antiproliferative activity of the novel, modified IFNs in crude bacterial extracts was also measured (Daudi cell line only).

Stimulation of Antibody-Dependent Cellular Cytotoxicity by novel, modified interferons (ADCC)

ADCC represents a cellular system which is immunologically specific the effect being mediated by antibody. There are several possible versions of this assay. $^{51}$Cr-labelled human red cells (GpA. Rh+ve) sensitised with anti-A antibody using the serum from a Group O individual were incubated with buffy coat cells from a Group O individual. Interferon was assessed by prior overnight incubation with buffy coat cells and its effects compared with those of parallel untreated controls (McCullagh et al. J. IFN Res., 3, 97, 1983).

Comparison of IFN protein expression, antiviral activity and antiproliferative activity in bacterial extracts Table 1 sets out the expression levels and antiproliferative and antiviral activities of the group II novel, modified IFNs in crude bacterial extracts. A range of activities may be given reflecting natural variation in a biological system or assay. The activity quoted is that which is regained after SDS/urea/mercaptoethanol treatment by diluting the extract in 1% human serum albumin, as above.

It may be seen in Table 1 that for the control, IFN-$\beta$, antiviral (AV) and antiproliferative (AP) activity vary over not more than a 4-fold range (>20 experiments). Examples of reduced AV activity in relation to AP activity and expression are IFNX407 and IFNX419 when compared with IFN-$\beta$. IFNX407 has ~2 to 9-fold lower AV activity and a <2-fold lower AP activity than IFN-$\beta$. An even greater differential is displayed by IFNX419, which has 7.7 to 57-fold lower AV activity than IFN-$\beta$, and a virtually unchanged AP activity.

TABLE 1

| Novel, modified interferon | IFNX No. | Expression (% of total cell protein) | EMC/Vero cell - Antiviral activity IU/Liter/OD$_{600}$ | Daudi cell - Antiproliferative activity U/ml = dilution at IC$_{50}$* |
|---|---|---|---|---|
| [$\beta^{9-56} \rightarrow \alpha_1^{7-54}$] | 407 | 5-10 | 2.3 × 10$^7$ | 1.9 × 10$^3$ |
| [$\beta^{44-56} \rightarrow \alpha_1^{42-54}$][Ser$^{17}$] | 408 | 3 | 0.46-2.0 × 10$^7$ | 1.1-1.6 × 10$^3$ |
| [$\beta^{42-56} \rightarrow \alpha_1^{40-54}$][Ser$^{17}$] | 409 | 3 | 0.4-1.0 × 10$^7$ | <10$^3$ |
| [$\beta^{2-7} \rightarrow \alpha_2^{1-5}$] [$\beta^{9-56} \rightarrow \alpha_1^{7-54}$] | 410 | 10-20 | 3.3-7.2 × 10$^7$ | 2 × 10$^3$ |
| [$\beta^{28-46} \rightarrow \alpha_1^{28-46}$] [Cys$^{17} \rightarrow$Ser][Met$^{31} \rightarrow$Lys] | 415 | 10-15 | 1.9 × 10$^9$ | 1.5 × 10$^5$ |
| [$\beta^{9-42} \rightarrow \alpha_1^{7-40}$] | 419 | 7 | 3.5-6.5 × 10$^6$ | 2.6 × 10$^3$ |
| [$\beta^{21-42} \rightarrow \alpha_1^{19-40}$] [Cys$^{17} \rightarrow$Ser] | 420 | <1.5 | 6.8-7.7 × 10$^6$ | <10$^3$ |
| IFN-$\beta$ control | — | 10 | 0.5-2.0 × 10$^8$ | 3.4 × 10$^3$ | n.d. = not done
*U/ml = Dilution of sample assayed for antiviral activity giving 50% inhibition of cell growth In conclusion, the novel, modified IFNs present in bacterial extracts display marked differences in relative AP and AV activity when compared with each other and with IFN-$\beta$. To determine more precisely the differences in biological activity between the novel IFNs and IFN-$\beta$, certain of the above examples were subjected to protein purification. The following assays were also designed to determine whether any of the novel IFNs displayed altered cell specificity.

The in vitro antiviral, antiproliferative and immunostimulating (ADCC) activities of purified novel, modified IFNs (a) Antiviral Table 2 compares the in vitro antiviral activity of purified IFNX415 with IFN-$\beta$ and IFNX805, against EMC virus in three different cell lines. IFNX415 displays an increase in antiviral activity only in the CHANG cell line (6 to 7-fold). Thus the antiviral specificity of this novel, modified IFN may be different from that of IFN-$\beta$ and IFNX805. Table 3 gives the result of a separate experiment in which purified IFNX407 and IFNX408 are compared with IFN-$\beta$. IFNX407 has substantially lower specific antiviral activity than IFN-$\beta$ on all three cell lines, while IFNX408 is similar to IFN-$\beta$.

TABLE 2

Antiviral Activity of Purified Novel, Modified Interferons
(Units/mg IFN Protein)

| IFNX No. | CELL LINE | | |
|---|---|---|---|
| | 17/1 | Chang | Vero |
| X415 | $1.8 \times 10^5$ | $3.1 \times 10^6$ | $3.3 \times 10^5$ |
| BETA | $1.3 \times 10^5$ | $5.1 \times 10^5$ | $7.6 \times 10^5$ |
| X805 | $7.6 \times 10^4$ | $4.4 \times 10^5$ | $4.2 \times 10^5$ |
| | RATIOS | | |
| X415/BETA | 1.4 | 6.1 | 0.4 |
| X415/X805 | 2.4 | 7.0 | 0.8 |
| X805/BETA | 0.6 | 0.9 | 0.6 |

TABLE 3

Antiviral activity of purified novel, modified interferons
Units/mg IFN protein

| IFNX No. | CELL LINE | | |
|---|---|---|---|
| | 17/1 | CHANG | VERO |
| X407 | $<5.1 \times 10^3$ | $9.5 \times 10^3$ | $1.9 \times 10^4$ |
| X408 | $4.2 \times 10^5$ | $4.6 \times 10^5$ | $1.2 \times 10^6$ |
| BETA | $1.9 \times 10^5$ | $7.2 \times 10^5$ | $9.1 \times 10^5$ |
| | RATIOS | | |
| X407/BETA | <0.02 | 0.01 | 0.02 |
| X408/BETA | 2.2 | 0.6 | 1.3 |

(b) Antiproliferative

Table 4 compares the in vitro antiproliferative activity of purified IFNX415 with IFN-β and IFNX805, on three different transformed cell lines IFNX805 and IFN-β display similar activities in all three cell lines, while IFNX415 has a significantly increased activity in the Daudi cell. Thus the in vitro antiproliferative specificity of IFNX415 may be different from that of IFN-β and IFNX805. Table 5 gives the result of a separate experiment in which purified IFNX407 and IFNX408 are compared with IFN-β. IFNX407 has substantially lower antiproliferative activity than IFN-β against HEP-2 and RD cell lines but similar activity to IFN-β against the Daudi cell line IFNX408 is similar to IFN-β.

TABLE 4

Antiproliferative Activity of Purified Novel, Modified Interferons
(Units/mg IFN Protein)

| IFNX No. | CELL LINE | | |
|---|---|---|---|
| | HEP-2 | RD | DAUDI |
| X415 | $2.2 \times 10^4$ | $2.2 \times 10^4$ | $1.9 \times 10^5$ |
| BETA | $8.9 \times 10^3$ | $6.5 \times 10^3$ | $1.4 \times 10^4$ |
| X805 | $5.4 \times 10^3$ | $4.3 \times 10^3$ | $1.2 \times 10^4$ |
| | RATIOS | | |
| X415/BETA | 2.5 | 3.4 | 13.6 |
| X415/X805 | 4.1 | 5.1 | 15.8 |
| X805/BETA | 0.6 | 0.7 | 0.9 |

TABLE 5

Antiproliferative activity of purified novel, modified interferons
Units/mg IFN protein

| IFNX No. | CELL LINE | | |
|---|---|---|---|
| | HEP-2 | RD | DAUDI |
| X407 | $<3.6 \times 10^1$ | $<2.0 \times 10^2$ | $1.0 \times 10^5$ |
| X408 | $8.9 \times 10^3$ | $1.0 \times 10^4$ | $3.1 \times 10^5$ |
| BETA | $1.3 \times 10^4$ | $1.9 \times 10^4$ | $2.5 \times 10^5$ |
| | RATIOS | | |
| X407/BETA | <0.002 | <0.01 | 0.4 |
| X408/BETA | 0.7 | 0.5 | 1.2 |

(c) Immunostimulating (ADCC)

Table 6 compares the in vitro activity of purified IFNX415 with IFN-β and IFNX805, as an effector of Antibody-Dependent Cellular Cytoxicity (ADCC) against human red cells. Overall, IFNX415, IFNX805 and IFN-β did not differ significantly in their ability to stimulate ADCC activity of buffy coat preparations from 5 group 0 donors. This is in contrast with the increased AV activity in CHANG cells and the increased AP activity in Daudi cells of IFNX415 (Tables 2 and 3). Table 7 gives the result of a separate experiment in which IFNX407 and IFNX408 are compared. The ADCC activity of IFNX407 was too low for accurate assessment. IFNX408 had slightly reduced specific activity compared with IFN-β.

TABLE 6

Immunomodulatory (ADCC) Activity of Purified Novel, Modified Interferons
(Units/mg IFN Protein)

| IFNX No. | DONOR | | | | |
|---|---|---|---|---|---|
| | 1 | 2 | 3 | 4 | 5 |
| X415 | $1.3 \times 10^3$ | $2.3 \times 10^3$ | $7.1 \times 10^2$ | $6.3 \times 10^3$ | $1.2 \times 10^3$ |
| BETA | $1.0 \times 10^3$ | $1.9 \times 10^3$ | $1.1 \times 10^2$ | $1.1 \times 10^4$ | $1.7 \times 10^3$ |
| X805 | $4.5 \times 10^2$ | $3.2 \times 10^2$ | $1.5 \times 10^2$ | $1.8 \times 10^3$ | $5.8 \times 10^2$ |
| | RATIOS | | | | |
| X415/BETA | 1.3 | 1.2 | 6.5 | 0.6 | 0.7 |
| X415/X805 | 2.9 | 7.2 | 4.7 | 3.5 | 2.1 |
| X805/BETA | 0.5 | 0.2 | 1.4 | 0.2 | 0.3 |

TABLE 7

Immunomodulatory (ADCC) activity of purified novel, modified interferons
Units/mg IFN Protein

| IFNX No. | DONOR | | | | | |
|---|---|---|---|---|---|---|
| | 1 | 2 | 3 | 4 | 5 | 6 |
| X407 | $<10^2$ | $<10^2$ | $<10^2$ | $<10^2$ | $<10^2$ | $<10^2$ |
| X408 | $1.8 \times 10^2$ | $6.2 \times 10^3$ | $2.6 \times 10^2$ | $1.3 \times 10^2$ | $1.6 \times 10^3$ | $9.1 \times 10^2$ |
| BETA | $1.5 \times 10^3$ | $2.4 \times 10^4$ | $9.3 \times 10^2$ | $3.0 \times 10^3$ | $4.0 \times 10^3$ | $2.6 \times 10^3$ |
| | RATIOS | | | | | |
| X407/BETA | <0.06 | <0.004 | <0.1 | <0.03 | <0.02 | <0.04 |
| X408/BETA | 0.1 | 0.3 | 0.3 | 0.4 | 0.4 | 0.4 |

Purification and Biological Properties of IFNX402 and IFNX404

1. Methods

The expressed IFN proteins were extracted from E.coli with the aid of sodium dodecyl sulphate (SDS) and purified by chromatography on AcA 44. IFNX401 had estimated purities of 70–90% based on polyacrylamide gel electrophoretic (PAGE) analysis.

The novel interferons were tested to determine its specific antiviral, antiproliferative and immunomodulatory activities. The following assay systems were employed:

(i) Antiviral assay
  (a) Cytopathic (CPE) assay with encephalomyocarditis (EMC) virus. This is a standard assay which measures the ability of interferon to protect cell monolayers against the cytopathic effect of EMC virus. The cell lines used were: Vero (African Green Monkey epithelial), WISH (amnion epithelial), MRC-5 (foetal lung fibroblast) and 17-1 (foetal lung fibroblast). Cell monolayers were established in 96 well flat-bottomed microtitre plates in DMEM medium containing 2% donor calf serum plus glutamine and antibiotics. Serial 1 in 2 dilutions of interferon were incubated with the cells at 37° for 18-24 hours, the supernatant discarded and an appropriate challenge dose of EMC virus in medium added. After incubation at 37° for a further 24 hours, the supernatants were discarded the monolayers fixed with formol/saline and stained with crystal violet. The plates were read visually to establish the dilution of interferon giving 50% inhibition of the cytopathic effect.
  (b) Plaque reduction assay—using Herpes simplex type 2 (HSV-2) virus with Vero (monkey) Chang (human) and MDBK (bovine cells). Confluent monolayers of cells were established in 96 well flat-bottomed microtitre plates. After incubation at 37° for 18 hours with dilutions of interferons, the cells were challenged with an appropriate number of plaque forming units of virus, overlaid with medium containing 0.5% carboxymethyl cellulose and incubated at 37° for 24 hours. After fixation and staining the plaques were counted microscopically and the counts expressed as a percentage of the mean maximum plaque counts in untreated control wells. Interferon titres are the reciprocal dilutions giving 50% reduction in plaque number/well.

(ii) Antiproliferative assay
  Daudi cells in Dulbecco's Modified Eagles Medium (DMEM) were seeded at $2 \times 10^5$/ml (200 μl) in 96 well tissue culture plates. Interferons were added at the time of seeding and cells incubated at 37° in a humidified 5% $CO_2$ atmosphere. After 22 hours tritiated thymidine was added and the cells incubated for a further 2 hours after which they were harvested on a Flow cell harvester washed and treated with 5% trichloroacetic acid. Acid insoluble radioactivity was counted and inhibition of thymidine incorporation was taken as a measure of the antiproliferative activity of interferon.

(iii) Immunomodulatory assay (Natural Killer (NK) Cell Activity)
  Buffy coat cells separated from human peripheral blood by Ficoll/Hypaque sedimentation were suspended in supplemented RPMI 1640 medium and incubated overnight at 37° with interferon dilutions. After washing to remove interferon these effector cells were incubated at 37° for a further 4 hours with $^{51}Cr$-labelled K562 cells at effector to target cell ratios of 20:1 or 10:1. (K562 is a human tumour-derived cell line). After centrifugation an aliquot of the supernatant was removed for measurement of released radioactivity. Maximum $^{51}Cr$ release was obtained by repeated freeze-thawing of a target cell suspension and a background control obtained by measurement of $^{51}Cr$ release from target cells incubated without effector cells. Results were expressed as percentage specific $^{51}Cr$ release:

$$\frac{\text{Test sample} - \text{background}}{\text{Maximum release} - \text{background}} \times 100$$

2. Results (i) Antiviral activities
  (a) CPE assay—EMC virus
    Table 8 lists the assay means for hybrid X401 and the recombinant-derived IFN-β measured against EMC virus in Vero and the four human cell lines. The activities are expressed in units/mg protein.
    From the individual interferon means in different cell types contained in Table 8 and from the summary pooled data across all cell types it is seen that IFNX402 and IFNX404 have consistently lower activities than IFN-β, the reduction being most severe with IFNX402. The pooled mean antiviral activity shown in the analysis of variance for IFNX402 is less than 1% that of IFN-β. The activity of IFNX404 is 5-15% of IFN-β.

TABLE 8

Antiviral activities of recombinant interferons against encephalomyocarditis virus (IFN units/mg protein)
Mean activities in each cell line

| PREPARATION | CELL LINE | | | | | POOLED MEAN | 95% CONFIDENCE LIMITS (u/mg) |
| | Vero | Chang | WISH | MRC-5 | 17-1 | | |
| --- | --- | --- | --- | --- | --- | --- | --- |
| IFN-β $\bar{x}$ | $1.5 \times 10^5$ | $5.2 \times 10^5$ | $8.4 \times 10^5$ | $1.5 \times 10^5$ | $7.1 \times 10^4$ | $2.4 \times 10^5$ u/mg | $1.5-3.9 \times 10^5$ |
| IFNX402 $\bar{x}$ | $2.5 \times 10^3$ | $4.1 \times 10^2$ | $4.8 \times 10^3$ | $4.9 \times 10^2$ | $3.3 \times 10^2$ | $1.1 \times 10^3$ u/mg | $0.6-2.1 \times 10^3$ |
| IFNX404 $\bar{x}$ | $2.6 \times 10^4$ | $1.8 \times 10^4$ | $4.8 \times 10^4$ | $5.8 \times 10^3$ | $2.3 \times 10^3$ | $8.9 \times 10^3$ u/mg | $5.4-14.8 \times 10^3$ |

($\bar{x}$ calculated based upon 3-5 assays)

For comparative purposes, the observed activities (in units/ml) of preparations of fibroblast IFN-β and leucocyte IFN-α are shown in Table 9. These natural interferons were not available in purified form and were used in the assays in dilute solutions containing large amounts of non-interferon protein. Thus, results with natural IFN-β and IFN-α cannot be quoted in units/mg and the results in Table 9 are not directly comparable with those of Table 8. Nevertheless, it can be seen that the activity of both natural interferons is sustained across the five cell lines within an interferon class with the exception that WISH cells appear slightly more sensitive to both IFN-β and IFN-α.

TABLE 9

Relative antiviral activities of natural interferon preparations against encephalomyocarditis virus in vero and human cell lines

| PREPARATION | Interferon units/ml CELL LINE | | | | |
|---|---|---|---|---|---|
| | Vero | Chang | WISH | MRC-5 | 17-1 |
| Fibroblast-derived $\beta$ x | $3.6 \times 10^4$ | $5.6 \times 10^4$ | $1.3 \times 10^5$ | $7.8 \times 10^4$ | $6.8 \times 10^4$ |
| Leucocyte-derived IFN-$\alpha$ x | $2.5 \times 10^2$ | $1.5 \times 10^2$ | $1.3 \times 10^3$ | 80 | 80 |

(b) Plaque reduction assays HSV-2

Similar estimates of antiviral activities obtained with HSV-2 by means of plaque reduction assays are given in Table 10. In this case the experiments were confirmed to the human Chang cells, primate Vero cells on bovine MDBK cells. IFNX402 and IFNX404 show reduced antiherpes activity in human and monkey cells. With the bovine cell line. IFNX404 shows reduced activity as it does in Chang and Vero, but surprisingly, the activity of IFNX402 in this cell line is unchanged from that of the IFN-$\beta$ parent. An analysis of variance confirmed that the observed reduction in activity for IFNX402 and X404 in Vero and Chang cells is highly significant as is the difference between the activity of IFNX402 in Chang and MDBK cells.

The pattern of natural IFN-$\beta$ and IFN-$\alpha$ against HSV-2 in these 3 cell lines is shown in Table 11, again expressed as units/ml rather than as specific activity as a result of impure IFNs. In contrast to some reported results from other laboratories, IFN-$\beta$ reacts reasonably well with our MDBK cell line, producing antiviral activity at about the same dilution as Vero or Chang cells. On the other hand, the IFN-$\alpha$ standard reacted substantially better than MDBK cells than with either Vero or Chang cells. In view of this control data, the reduced activity of IFNX402 in Chang and Vero cells and retained activity in MDBK cells represents a pattern of response in these cell lines which is similar to that obtained with natural IFN-$\alpha$.

TABLE 10

Antiviral activities of recombinant interferons against HSV-2 determined by plaque reduction assay

| PREPARATION | Interferon units/mg protein CELL LINE | | |
|---|---|---|---|
| | Vero | Chang | MDBK |
| IFN-$\beta$ x | $1.2 \times 10^5$ | $4.7 \times 10^5$ | $2.5 \times 10^5$ |
| IFNX402 x | $1.1 \times 10^3$ | $1.3 \times 10^3$ | $3.4 \times 10^5$ |
| IFNX404 x | $7.0 \times 10^3$ | $9.9 \times 10^3$ | $4.4 \times 10^3$ |

TABLE 11

Relative antiviral activity of natural interferons against HSV-2 in monkey, human and bovine cells determined by plaque reduction

| PREPARATION | Interferon units/ml CELL LINE | | |
|---|---|---|---|
| | Vero | Chang | MDBK |
| Fibroblast-derived IFN-$\beta$ x | $2.6 \times 10^4$ | $9.3 \times 10^4$ | $1.9 \times 10^4$ |
| Leucocyte-derived IFN-$\alpha$ x | 59 | 90 | $6.8 \times 10^3$ |

Summarizing the results of antiviral activity with RNA and DNA viruses in relevant cell types, Table 12 lists the activities of the recombinant and natural interferons against EMC and HSV-2 in Chang and Vero cells (data from Tables 8–11). There is no indication from these results of preferential activity of IFNX402 against one or other of the 2 virus types. The results from the 2 sets of assays are remarkably similar and are not significantly different. Thus the pooled mean antiviral activity against EMC virus shown in the analysis of variance to Table 8 is equally valid as an estimate of antiherpes activity and can be used as an overall indicator of specific antiviral activity of IFNX402.

TABLE 12

Relative antiviral activity against encephalomyocarditis virus and HSV-2 for recombinant and natural interferons assayed in human and monkey cells
Recombinant interferons (unit/mg protein)

| IFN Preparation | Pooled mean activity EMC virus (from Table 1 analysis) | Pooled mean activity HSV-2 Vero and Chang cells |
|---|---|---|
| IFN-$\beta$ | $2.4 \times 10^5$ | $3.5 \times 10^5$ |
| IFNX402 | $1.1 \times 10^3$ | $1.2 \times 10^3$ |
| IFNX404 | $8.9 \times 10^3$ | $8.5 \times 10^3$ |

(c) Comparative antiviral data with an atypical Chang cell line

One line of Chang conjunctival cells maintained in high passage (approx. X 160) has undergone a mutational change such that it is approximately 3 times more sensitive to IFN-$\beta$ than the normal low passage Chang cells which we have used in routine assays. At the same time the atypical high passage Chang cells recognize and respond to IFN-$\alpha$ with a 100-fold increase in sensitivity compared to the parental low passage Chang cells. Comparative ratios of antiviral activity in high and low passage Chang cells can therefore be used to indicate a degree of $\alpha$-like property in a particular recombinant.

The results of profiling the recombinant IFNX molecules in this way is shown in Table 13. IFNX402 is prominent in demonstrating $\alpha$-like activity.

(ii) Antiproliferative activity

The various recombinant interferons were assayed, for growth inhibitory activity against Daudi lymphoblastoid cells, in at least 4 replicate assays with each interferon. The mean results of these assays are given in Table 14, activities being expressed as the protein concentration required to produce a 50% inhibition of maximum thymidine incorporation in untreated control cells (Inhibitory Dose$_{50}$). The poorly antiviral IFNX402 can be seen to have an identical growth regulating activity to the IFN-$\beta$ parent. In contrast IFNX404 has lost growth regulating activity.

TABLE 13

Antiviral activities of recombinant and natural interferons in atypical Chang cells

| | Chang$^A$ (High passage) | Chang (Routine low passage) | Ratio ChA/Ch |
|---|---|---|---|
| | Units/mg | | |
| IFN-$\beta$ | $1.6 \times 10^6$ | $5.2 \times 10^5$ | 3 |
| IFNX402 | $1.3 \times 10^6$ | $4.1 \times 10^2$ | 3170 |
| IFNX404 | $5.3 \times 10^4$ | $1.8 \times 10^4$ | 3 |
| | Units/ml | | |
| Fibroblast IFN-$\beta$ | $1.7 \times 10^5$ | $5.6 \times 10^4$ | 3 |

TABLE 13-continued

Antiviral activities of recombinant and natural interferons in atypical Chang cells

| | Chang[4] (High passage) | Chang (Routine low passage) | Ratio ChA/Ch |
|---|---|---|---|
| Leucocyte IFN-α | $3.4 \times 10^4$ | $1.5 \times 10^2$ | 226 |

TABLE 14

Antiproliferative activity of recombinant interferons assayed in Daudi human lymphoblastoid cells
Inhibitory Dose$_{50}$ (μg/ml)

| PREPA-RATION | No. of replicate assays (n) | Corrected Mean ID$_{50}$ | 95% Confidence Limits |
|---|---|---|---|
| IFN-β | 4 | 3.8 | 1.5–9.8 |
| IFNX402 | 6 | 3.2 | 1.4–6.9 |
| IFNX404 | 4 | 44.7 | 17.4–114.8 |

(iii) Immunomodulatory activity—NK assay

The recombinant interferons were also repeatedly assayed for ability to enhance natural killer (NK) cell activity, a total of 9–11 assays contributing to the results which are shown in Table 15. In a similar fashion to the antiproliferative activity, the specific NK stimulating activity is expressed as the protein dose concentration producing a 50% effect (Stimulating Dose$_{50}$).

IFNX402 has substantially lost NK stimulating activity, being about 35-fold less active than IFN-β parent. IFNX404 has also less activity but only by a factor of 4. These differences are significant as shown in the analysis of variance.

TABLE 15

Immunostimulant activities of recombinant interferons assayed with human NK cells

| PREPA-RATION | No. of replicate assays (n) | Corrected Mean SD$_{50}$ | 95% Confidence Limits |
|---|---|---|---|
| IFN-β | 11 | 3.4 | 2.1–5.4 |
| IFNX402 | 9 | 117.0 | 339 |
| IFNX404 | 10 | 15.1 | 9.3–24.5 |

3. Conclusions

Mean specific activities for the antiviral, antiproliferative and immunomodulatory properties of each interferon are summarized in Table 16. (It should be noted that activity varies directly with the figures taken from antiviral assays but inversely with the figures quoted from ID$_{50}$ and SD$_{50}$ assays). For convenience these results have been indexed relative to the IFN-β parent in the lower half of Table 16.

TABLE 16

Comparative summary of biological data for recombinant and natural interferons

| PREPA-RATION | Specific antiviral activity (μ/mg) | Specific antiproliferative activity (ID$_{50}$ μm/ml$^{-1}$) | Specific immunostimulant activity (SD$_{50}$ μg/ml$^{-1}$) |
|---|---|---|---|
| IFN-β | $2.4 \times 10^5$ | 3.8 | 3.4 |
| IFNX402 | $1.1 \times 10^3$ | 3.2 | 195.0 |
| IFNX404 | $8.9 \times 10^3$ | 44.7 | 15.1 |
| Indexed results (IFN-β = 100) | | | |
| IFN-β | 100 | 100 | 100 |
| IFNX402 | 0.5 | 100 (118) | 3 |
| IFNX404 | 3.7 | 9 | 23 |

Figures in brackets indicate actual calculated index where it is not significantly different from 100. In all other cases, differences from 100 are significant.
IFNX402 has identical antiproliferative activity to IFN-β but has dramatically reduced antiviral and immunostimulant activities.
IFNX404 has reduced efficacy in all 3 classes of biological assay.

The most surprising result to come out of these analyses is the separation of activities achieved with IFNX402. This finding was unexpected but it is of great interest since the presence of full antiproliferative activity in a molecule which has major reductions in its other properties might be effective as an anti-tumour agent but have reduced toxicity and lack unwanted side effects.

The major conclusions summarized above are based on results in human cell systems. MDBK (bovine) and Chang[4] (atypical human) showed increased sensitivity to IFNX402 such that the decrease in antiviral properties of this hybrid seen in normal human cells are not seen with these heterologous or atypical systems. As a result, the ratio in antiviral activity between MDBK and human or monkey cells (Table 10) or between Chang[4] and the normal Chang cells (Table 13) is dramatically large with the IFNX402 preparation and clearly different from that of IFN-β or any other hybrids. An elevation in the MDBK/Chang or Chang[4]/Chang ratio is characteristic of natural leucocyte IFN-α (Tables 11 and 13). In this respect the IFNX402 hybrid has an "alpha-like" profile.

Pharmaceutical formulation and administration

The novel, modified interferons of the present invention can be formulated by methods well known for pharmaceutical compositions, wherein the active interferon is combined in admixture with a pharmaceutically acceptable carrier substance, the nature of which depends on the particular mode of administration being used. Remington's Pharmaceutical Sciences by E W. Martin, hereby incorporated by reference, describes compositions and formulations suitable for delivery of the interferons of the present invention. For instance, parenteral formulations are usually injectable fluids that use physiologically acceptable fluids such as saline, balanced salt solutions, or the like as a vehicle. Oral formulations may be solid, e.g. tablet or capsule, or liquid solutions or suspensions.

The novel, modified interferons of the invention may be administered to humans or other animals on whose cells they are effective in various ways such as orally, intravenously, intramuscularly, intraperitoneally, intranasally, intradermally or subcutaneously. Administration of the interferon composition is indicated for patients with malignancies or neoplasms, whether or not immunosuppressed or in patients requiring immunomodulation, or antiviral treatment. Dosage and dose rates may parallel those employed in conventional therapy with naturally occurring interferons—approximately $10^5$ to $10^8$ units daily. Dosages significantly above or below these levels may be indicated in long term administration or during acute short term treatment. A novel, modified interferon may be combined with other treatments or used in association with other chemotherapeutic or chemopreventive agents for providing therapy against the above mentioned diseases and conditions, or other conditions against which it is effective.

Modifications of the above described modes for carrying out the invention such as without limitation, use of alternative vectors, alternative expression control systems, and alternative host micro-organisms and other therapeutic or related uses of the novel interferons, that are obvious to those of ordinary skill in the biotechnology, pharmaceutical, medical and/or related fields are intended to be within the scope of the following claims.

We claim:

1. A modified beta interferon comprising a beta interferon wherein amino acids 2 to 7 of said beta interferon are replaced by amino acids 1 to 5 of alpha 2 interferon and amino acids 9 to 56 of said beta interferon are replaced with amino acids 7 to 54 of alpha 1 interferon.

2. A modified beta interferon comprising a beta interferon wherein amino acids 9 to 56 of said beta interferon are replaced with amino acids 7 to 54 of alpha 1 interferon.

3. A modified beta interferon comprising a beta interferon wherein amino acids 9 to 56 of said beta interferon are replaced with amino acids 7 to 54 of alpha 1 interferon except that the leucine at position 15 of said alpha 1 interferon is replaced by cysteine so that the modified beta interferon has cysteine at position 17.

4. A modified beta interferon comprising a beta interferon wherein amino acids 44 to 56 of said beta interferon are replaced with amino acids 42 to 54 of alpha 1 interferon and the cysteine at position 17 of said beta interferon is replaced by serine.

5. A modified beta interferon comprising a beta interferon wherein amino acids 9 to 42 of said beta interferon are replaced with amino acids 7 to 40 of alpha 1 interferon.

6. A modified beta interferon comprising a beta interferon wherein amino acids 21 to 42 of said beta interferon are replaced with amino acids 19 to 40 of alpha 1 interferon and the cysteine at position 17 of said beta interferon is replaced by serine.

7. A modified beta interferon wherein amino acids 28 to 46 of beta interferon are replaced with amino acids 28 to 46 of alpha 1 interferon, with the exception that the methionine at position 31 of said alpha 1 interferon is replaced by lysine, and the cysteine at position 17 of said beta interferon is replaced by serine.

8. A pharmaceutical composition for treating viral infections in an animal comprising an effective therapeutic amount of the modified beta interferon of claim 1 admixed with a pharmaceutically acceptable carrier.

9. A pharmaceutical composition for treating viral infections in an animal comprising an effective therapeutic amount of the modified beta interferon of claim 2 admixed with a pharmaceutically acceptable carrier.

10. A pharmaceutical composition for regulating cell growth in an animal comprising an effective therapeutic amount of the modified beta interferon of claim 3 admixed with a pharmaceutically acceptable carrier.

11. A pharmaceutical composition for treating viral infections in an animal comprising an effective therapeutic, amount of the modified beta interferon of claim 4 admixed with a pharmaceutically acceptable carrier.

12. A pharmaceutical composition for regulating cell growth in an animal comprising an effective therapeutic amount of the modified beta interferon of claim 5 admixed with a pharmaceutically acceptable carrier.

13. A pharmaceutical composition for treating viral infections in an animal comprising an effective therapeutic amount of the modified beta interferon of claim 6 admixed with a pharmaceutically acceptable carrier.

14. A pharmaceutical composition for treating viral infections or regulating cell growth, or for stimulating the immune system in an animal comprising an effective therapeutic amount of the modified beta interferon of claim 7 admixed with a pharmaceutically acceptable carrier.

15. A method of treating viral infections in an animal in need of such treatment comprising the administration of an effective therapeutic amount of a modified beta interferon of claim 7.

16. A method of regulating cell growth in an animal in need of such treatment comprising the administration of an effective therapeutic amount of modified beta interferon of claim 7.

17. A method of regulating the immune system in an animal in need of such treatment comprising the administration of an effective therapeutic amount of a modified beta interferon of claim 7.

* * * * *